(12) United States Patent
Hause

(10) Patent No.: US 11,351,241 B2
(45) Date of Patent: Jun. 7, 2022

(54) UNIVERSAL INFLUENZA VACCINE

(71) Applicant: Cambridge Technologies LLC, Worthington, MN (US)

(72) Inventor: Ben Hause, Slayton, MN (US)

(73) Assignee: Cambridge Technologies LLC, Worthington, MN (US)

( * ) Notice: Subject to any disclaimer, the term of this patent is extended or adjusted under 35 U.S.C. 154(b) by 22 days.

(21) Appl. No.: 16/711,873

(22) Filed: Dec. 12, 2019

(65) Prior Publication Data

US 2020/0188505 A1    Jun. 18, 2020

Related U.S. Application Data

(60) Provisional application No. 62/778,409, filed on Dec. 12, 2018.

(51) Int. Cl.
| | | |
|---|---|---|
| A61K 39/12 | (2006.01) | |
| A61P 31/16 | (2006.01) | |
| A61K 39/00 | (2006.01) | |

(52) U.S. Cl.
CPC ............. *A61K 39/12* (2013.01); *A61P 31/16* (2018.01); *A61K 2039/5156* (2013.01); *A61K 2039/552* (2013.01); *A61K 2039/58* (2013.01); *C12N 2710/14034* (2013.01); *C12N 2710/14042* (2013.01)

(58) Field of Classification Search
None
See application file for complete search history.

(56) References Cited

U.S. PATENT DOCUMENTS

| | | | | |
|---|---|---|---|---|
| 6,103,526 | A * | 8/2000 | Smith .................. | C07K 14/005 435/348 |
| 7,910,112 | B2 | 3/2011 | Poulet et al. | |
| 7,993,652 | B2 | 8/2011 | Neirynck et al. | |
| 8,399,246 | B2 | 3/2013 | Hu et al. | |
| 9,050,290 | B2 | 6/2015 | Smith et al. | |
| 9,115,201 | B2 | 8/2015 | Yusibov et al. | |
| 9,695,446 | B2 | 7/2017 | Mangeot et al. | |
| 10,080,794 | B2 | 9/2018 | Perez et al. | |
| 2007/0207168 | A1* | 9/2007 | Daemmgen .......... | C07K 14/005 424/209.1 |
| 2007/0275014 | A1 | 11/2007 | Yusibov et al. | |
| 2011/0045540 | A1 | 2/2011 | Hu et al. | |
| 2013/0122025 | A1 | 5/2013 | Harris et al. | |
| 2016/0303223 | A1 | 10/2016 | Galarza et al. | |
| 2020/0188505 | A1* | 6/2020 | Hause ..................... | A61P 31/16 |

FOREIGN PATENT DOCUMENTS

| | | |
|---|---|---|
| CA | 2410297 | 6/2002 |
| CN | 105457023 | 4/2016 |
| EP | 0830141 | 6/2003 |
| EP | 0733113 | 5/2007 |
| EP | 1984405 | 10/2008 |
| EP | 1119612 | 7/2010 |
| EP | 2211901 | 5/2013 |
| WO | 2010125461 | 11/2010 |
| WO | 2010144797 | 12/2010 |
| WO | 2016137929 | 9/2016 |
| WO | 2019169231 | 9/2019 |
| WO | 2019191261 | 10/2019 |

OTHER PUBLICATIONS

Influenza Strain Details for A/Johannesburg/33/94(H3N2); 2006.*
Sultana et al. (Vaccine. 2014; 32: 2225-2230).*
Mottershead et al. (Biochemical and Biophysical Research Communications. 1997; 238: 717-722).*
Johansson et al. (PNAS. 1994; 91: 2358-2361).*
Rajao et al. (Virology. 2016; 491: 79-88).*
Vincent et al. (Veterinary Microbiology. 2017; 206: 35-44).*
International Search Report and Written Opinion in corresponding PCT/US2019/065883, dated Apr. 6, 2020.
Extended Search Report in corresponding European Patent Application Serial No. 19215483.9, dated May 12, 2020.
Mather, et al., "Expression of influenza neuraminidase in baculovirus-infected cells", Virus Research, 26 (1992) 127-139.
Quan, et al., "Influenza MI VLPs containing neuraminidase induce heterosubtypic cross-protection", Virology 430 (2012)127-135.
Park, et al., "Protective efficacy of erode virusdike particle vaccine against HPAI H5N1 in chickens and its application on DIVA strategy", Influenza and Other Respiratory Viruses, Jun. 2012, 7(3), 340-348.
Eichelberger, et al., "Neuraminidase as an influenza vaccine antigen: a low hanging fruit, ready for picking to improve vaccine effectiveness", Current Opinion in Immunology 2018, 53:38-44.
Najafi, et al., "Baculoviral Expression of Influenza A Virus (H1N1 New Caledonia) Neuraminidase in Insect Cells", Iranian Journal of Virology 2012;6(2): 12-17.
Cox, "Recombinant protein vaccines produced in insect cells", Protein Sciences Corporation, Jan. 25, 2013.
Wohlbold, et al., "Vaccination with Adjuvanted Recombinant Neuraminidase Induces Broad Heterologous, but Not Heterosubtypic, Cross-Protection against Influenza Virus Infection in Mice", mbio. asm.org, Mar./Apr. 2015 vol. 6 Issue 2 e02556-14.

(Continued)

Primary Examiner — Shanon A. Foley
(74) Attorney, Agent, or Firm — Hovey Williams LLP

(57) ABSTRACT

Immunogenic compositions for inducing a universal immune response to influenza, and particularly influenza A, by eliciting anti-neuraminidase antibodies which provide protection against heterologous influenza infection. Compositions comprising recombinant baculovirus expression vectors expressing neuraminidase in cultured insect cells dispersed in a pharmaceutically-acceptable carrier comprising insect cell culture media, and optional adjuvant. Methods of inducing immune responses against influenza, and particularly influenza A, by eliciting anti-neuraminidase antibodies in a host animal susceptible to infection.

28 Claims, 11 Drawing Sheets

Specification includes a Sequence Listing.

(56) References Cited

OTHER PUBLICATIONS

Dalakouras, et al., "Development of recombinant protein-based influenza vaccine: Expression and affinity purification of H1N1 influenza virus neuraminidase", J of Chromatography A, vol. 1136, Issue 1, Dec. 8, 2006, pp. 48-56 (abstract attached).

Pour, et al., "Construction of recombinant fusion protein of influenza, a virus neuraminidase and heat shock protein 70 gene: expression in baculovirus and bioactivity", J. Medicine and Life, vol. 8, Special Issue 4, 2015, pp. 189-195.

Van Epps, "Influenza: exposing the true killer", J. Exp. Med., 2006, 203(4), p. 803.

Haden, et al., "Assessing production parameters and economic impact of swine influenza, PRRS and Mycoplasma hyopneumoniae on finishing pigs in a large production system", 2012 Proceedings AASV Annual Meeting, pp. 75-76.

Donovan, "Influenza isolate selection methodology for timely autogenous vaccine use", 2008, Proceedings. Amer Assoc Swine Vet Conf, pp. 557-561.

Smith, et al., "Origins and evolutionary genomics of the 2009 swine-origin H1N1 influenza A epidemic", Nature, 2009, 459, pp. 1122-1125.

Markowska-Daniel, et al., "The influence of age and maternal antibodies on the postvaccinal response against swine influenza viruses in pigs", Vet Immunol Immunopathol., 2011, 142, pp. 81-86.

Johansson, et al., "Dissociation of influenza virus hemagglutinin and neuraminidase eliminates their intravirionic antigenic competition", J. Virol., 1993, 67(10), pp. 5721-5723.

Marcelin, et al., "Contribution of antibody production against neuraminidase to the protection afforded by influenza vaccines". Rev Med Virol., 2012, 22(4), pp. 267-279.

Gao et al., The genomic evolution of H1 influenza A viruses from swine detected in the United States between 2009 and 2016, Journal of General Virology, 2017; 98:2001-2010.

Walia et al., Regional patterns of genetic diversity in swine influenza A viruses in the United States from 2010 to 2016, Influenza Other Respi Viruses., 2019;13:262-273.

Bolton et al., Antigenic evolution of H3N2 influenza A viruses in swine in the United States from 2012 to 2016, Influenza Other Resp Viruses. 2019;13:83-90.

Notice of Reasons for Refusal in corresponding Japanese Patent Application Serial No. 2019-224243, dated Sep. 3, 2021 (English translation attached).

Liu, et al., "Cross-Reactive Neuraminidase-Inhibiting Antibodies Elicited by Immunization with Recombinant Neuraminidase Proteins of H5N1 and Pandemic H1N1 Influenza A Viruses", J Virology, 2015, 89(14), pp. 7224-7234.

Office Action in corresponding Canadian Patent Application Serial No. 3064760, dated Oct. 13, 2021.

* cited by examiner

SEQUENCE LISTING

```
<160> NUMBER OF SEQ ID NOS: 6

<210> SEQ ID NO 1
<211> LENGTH: 1410
<212> TYPE: DNA
<213> ORGANISM: Influenza A virus
<220> FEATURE:
<221> NAME/KEY: CDS
<222> LOCATION: (1)..(1410)
<220> FEATURE:
<221> NAME/KEY: misc_feature
<222> LOCATION: (1)..(1410)
<223> OTHER INFORMATION: A/swine/Iowa/A01782229/2016 (H1N1)
      neuraminidase
```

<400> SEQUENCE: 1

```
atg aat aca aat caa aga ata ata acc att ggg aca ttt tgc atg ata      48
Met Asn Thr Asn Gln Arg Ile Ile Thr Ile Gly Thr Phe Cys Met Ile
1               5                   10                  15 gtt gga ata gtc agt cta ttg tta cag ata gga aac ata gtc tcg tta      96
Val Gly Ile Val Ser Leu Leu Leu Gln Ile Gly Asn Ile Val Ser Leu
                20                  25                  30 tgg att agc cat tca att cag acc gga tgg gaa aat cac act ggg atg     144
Trp Ile Ser His Ser Ile Gln Thr Gly Trp Glu Asn His Thr Gly Met
            35                  40                  45 tgc aac caa agt gtt att aca tat gta aat aac aca tgg gtg aac cga     192
Cys Asn Gln Ser Val Ile Thr Tyr Val Asn Asn Thr Trp Val Asn Arg
        50                  55                  60 act tat gtg aac att agc aat atc aaa att gct act ata cag gat gtg     240
Thr Tyr Val Asn Ile Ser Asn Ile Lys Ile Ala Thr Ile Gln Asp Val
65                  70                  75                  80 act ccg att ata cta gcc ggc aat tca cca ctt tgc cca gta agt ggg     288
Thr Pro Ile Ile Leu Ala Gly Asn Ser Pro Leu Cys Pro Val Ser Gly
                85                  90                  95 tgg gct gta tac agc aaa gac aat agc ata agg att ggt tct aaa ggg     336
Trp Ala Val Tyr Ser Lys Asp Asn Ser Ile Arg Ile Gly Ser Lys Gly
                100                 105                 110 gac att ttt gtc ata aga gaa cca ttc att tca tgc tct caa ttg gaa     384
Asp Ile Phe Val Ile Arg Glu Pro Phe Ile Ser Cys Ser Gln Leu Glu
            115                 120                 125 tgc aga acc ttc ttt ctg acc caa ggt gct ttg cta aat gac aaa cat     432
Cys Arg Thr Phe Phe Leu Thr Gln Gly Ala Leu Leu Asn Asp Lys His
        130                 135                 140 tct aat gga acc gtc aag gac agg agt ccc tat aga acc ctg atg agc     480
Ser Asn Gly Thr Val Lys Asp Arg Ser Pro Tyr Arg Thr Leu Met Ser
145                 150                 155                 160 tgc ccc atc ggt gaa gcc cca tct ccg tac aac tca agg ttc gaa tca     528
Cys Pro Ile Gly Glu Ala Pro Ser Pro Tyr Asn Ser Arg Phe Glu Ser
                165                 170                 175 gtt gct tgg tca gca agt gca tgt cat gat ggg atg gga tgg cta aca     576
Val Ala Trp Ser Ala Ser Ala Cys His Asp Gly Met Gly Trp Leu Thr
                180                 185                 190 atc ggg gtc tct ggt cca gat aat gga gca gta gct gtt tta aaa tac     624
Ile Gly Val Ser Gly Pro Asp Asn Gly Ala Val Ala Val Leu Lys Tyr
            195                 200                 205 aac ggt ata ata aca gat aca ata aaa agt tgg aga aac aaa ata tta     672
Asn Gly Ile Ile Thr Asp Thr Ile Lys Ser Trp Arg Asn Lys Ile Leu
        210                 215                 220 aga aca caa gag tca gaa tgt gtt tgt atg aac ggt tct tgt ttt act     720
Arg Thr Gln Glu Ser Glu Cys Val Cys Met Asn Gly Ser Cys Phe Thr
225                 230                 235                 240 gta tta act gat ggc cca agc aat ggg caa gcc tcg tac aaa ata ttt     768
Val Leu Thr Asp Gly Pro Ser Asn Gly Gln Ala Ser Tyr Lys Ile Phe
                245                 250                 255 aaa gtg gaa aaa ggg aaa ata att aag tca att gag ctg gat gcc ccc     816
Lys Val Glu Lys Gly Lys Ile Ile Lys Ser Ile Glu Leu Asp Ala Pro
                260                 265                 270 aat tac cac tat gaa gaa tgc tca tgc tat cct gat aca ggc aaa gtt     864
Asn Tyr His Tyr Glu Glu Cys Ser Cys Tyr Pro Asp Thr Gly Lys Val
            275                 280                 285 atg tgt gtt tgc aga gac aat tgg cat gcc tcg aac cgg cca tgg gtc     912
Met Cys Val Cys Arg Asp Asn Trp His Ala Ser Asn Arg Pro Trp Val
        290                 295                 300 tct ttc aat cag aat ctt gac tat caa ata gga tac ata tgc agt gga     960
```

```
                                      Ser Phe Asn Gln Asn Leu Asp Tyr Gln Ile Gly Tyr Ile Cys Ser Gly
                                      305                 310                 315                 320 gtt ttc ggt gat aac cct cgt tcc act gat ggg aag ggc aat tgt ggc              1008
Val Phe Gly Asp Asn Pro Arg Ser Thr Asp Gly Lys Gly Asn Cys Gly
                        325                 330                 335 cca gta ctt tct aat ggg gca aat gga gtg aaa gga ttc tca tat aga              1056
Pro Val Leu Ser Asn Gly Ala Asn Gly Val Lys Gly Phe Ser Tyr Arg
                340                 345                 350 tat ggt aat ggt gtt tgg ata gga aga act aag agt atc aac tcc aga              1104
Tyr Gly Asn Gly Val Trp Ile Gly Arg Thr Lys Ser Ile Asn Ser Arg
        355                 360                 365 agt gga ttt gaa atg att tgg gat cca aat ggg tgg act gaa act gat              1152
Ser Gly Phe Glu Met Ile Trp Asp Pro Asn Gly Trp Thr Glu Thr Asp
370                 375                 380 agt agt ttt tct atg aag cag gac att ata gca ttg gat gat tgg tca              1200
Ser Ser Phe Ser Met Lys Gln Asp Ile Ile Ala Leu Asp Asp Trp Ser
385                 390                 395                 400 gga tac agt gga agt ttt gtc caa cat ccg gaa tta aca gga atg aat              1248
Gly Tyr Ser Gly Ser Phe Val Gln His Pro Glu Leu Thr Gly Met Asn
                405                 410                 415 tgc ata agg cct tgt ttc tgg gtg gag cta atc aga ggg caa ccc aag              1296
Cys Ile Arg Pro Cys Phe Trp Val Glu Leu Ile Arg Gly Gln Pro Lys
            420                 425                 430 gaa agc aca atc tgg gct agc gga agc agc atc tct ttc tgt ggc gta              1344
Glu Ser Thr Ile Trp Ala Ser Gly Ser Ser Ile Ser Phe Cys Gly Val
                435                 440                 445 aat agt gaa acc gca aac tgg tca tgg cca gac ggg gct att ctg cca              1392
Asn Ser Glu Thr Ala Asn Trp Ser Trp Pro Asp Gly Ala Ile Leu Pro
450                 455                 460 ttc gcc att gac aag tag                                                       1410
Phe Ala Ile Asp Lys
465

<210> SEQ ID NO 2
<211> LENGTH: 469
<212> TYPE: PRT
<213> ORGANISM: Influenza A virus
<220> FEATURE:
<221> NAME/KEY: MISC_FEATURE
<222> LOCATION: (1)..(469)
<223> OTHER INFORMATION: expressed N1 subt Cys Arg Thr Phe Phe Leu Thr Gln Gly Ala Leu Leu Asn Asp Lys His
130                 135                 140

Ser Asn Gly Thr Val Lys Asp Arg Ser Pro Tyr Arg Thr Leu Met Ser
145                 150                 155                 160

Cys Pro Ile Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
            180                 185                 190

Ile Gly Val Ser Gly Pro Asp Asn Gly Ala Val Ala Val Leu Lys Tyr
        195                 200                 205

Asn Gly Ile Ile Thr Asp Thr Ile Lys Ser Trp Arg Asn Lys Ile Leu
210                 215                 220

Arg Thr Gln Glu Ser Glu Cys Val Cys Met Asn Gly Ser Cys Phe Thr
225                 230                 235                 240

Val Leu Thr Asp Gly Pro Ser Asn Gly Gln Ala Ser Tyr Lys Ile Phe
                245                 250                 255

Lys Val Glu Lys Gly Lys Ile Ile Lys Ser Ile Glu Leu Asp Ala Pro
            260                 265                 270

Asn Tyr His Tyr Glu Glu Cys Ser Cys Tyr Pro Asp Thr Gly Lys Val
        275                 280                 285

Met Cys Val Cys Arg Asp Asn Trp His Ala Ser Asn Arg Pro Trp Val
290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Ser Thr Asp Gly Lys Gly Asn Cys Gly
                325                 330                 335

Pro Val Leu Ser Asn Gly Ala Asn Gly Val Lys Gly Phe Ser Tyr Arg
            340                 345                 350

Tyr Gly Asn Gly Val Trp Ile Gly Arg Thr Lys Ser Ile Asn Ser Arg
        355                 360                 365

Ser Gly Phe Glu Met Ile Trp Asp Pro Asn Gly Trp Thr Glu Thr Asp
370                 375                 380

Ser Ser Phe Ser Met Lys Gln Asp Ile Ile Ala Leu Asp Asp Trp Ser
385                 390                 395                 400

Gly Tyr Ser Gly Ser Phe Val Gln His Pro Glu Leu Thr Gly Met Asn
                405                 410                 415

Cys Ile Arg Pro Cys Phe Trp Val Glu Leu Ile Arg Gly Gln Pro Lys
            420                 425                 430

Glu Ser Thr Ile Trp Ala Ser Gly Ser Ser Ile Ser Phe Cys Gly Val
        435                 440                 445

Asn Ser Glu Thr Ala Asn Trp Ser Trp Pro Asp Gly Ala Ile Leu Pro
450                 455                 460

Phe Ala Ile Asp Lys
465

<210> SEQ ID NO 3
<211> LENGTH: 1410
<212> TYPE: DNA
<213> ORGANISM: Influenza A virus
<220> FEATURE:
<221> NAME/KEY: CDS
<222> LOCATION: (1)..(1410)
<220> FEATURE:
<221> NAME/KEY: misc_feature
<222> LOCATION: (1)..(1410)
<223> OTHER INFORMATION: A/swine/Oklahoma/A01730659/2016 (H1N2)
      neuraminidase

<400> SEQUENCE: 3

| | | | | | | | | | | | | | | | | |
|---|---|---|---|---|---|---|---|---|---|---|---|---|---|---|---|---|
| atg | aat | cca | aat | caa | aag | ata | ata | aca | att | ggc | tct | gtt | tct | ctc | atc | 48 |
| Met | Asn | Pro | Asn | Gln | Lys | Ile | Ile | Thr | Ile | Gly | Ser | Val | Ser | Leu | Ile | |
| 1 | | | | 5 | | | | | 10 | | | | | 15 | | |

| att | gcc | aca | ata | tgc | ttc | ctt | atg | caa | att | gcc | atc | ctg | gtg | act | act | 96 |
|---|---|---|---|---|---|---|---|---|---|---|---|---|---|---|---|---|
| Ile | Ala | Thr | Ile | Cys | Phe | Leu | Met | Gln | Ile | Ala | Ile | Leu | Val | Thr | Thr | |
| | | | 20 | | | | | 25 | | | | | 30 | | | |

| gta | aca | ctg | cat | ttc | aag | caa | cat | aat | tgc | gac | tcc | tcc | cca | aac | aac | 144 |
|---|---|---|---|---|---|---|---|---|---|---|---|---|---|---|---|---|
| Val | Thr | Leu | His | Phe | Lys | Gln | His | Asn | Cys | Asp | Ser | Ser | Pro | Asn | Asn | |
| | 35 | | | | | 40 | | | | | 45 | | | | | |

| cat | gta | atg | ttt | tgt | gaa | cca | aca | ata | ata | gaa | aga | aac | aaa | acg | gag | 192 |
|---|---|---|---|---|---|---|---|---|---|---|---|---|---|---|---|---|
| His | Val | Met | Phe | Cys | Glu | Pro | Thr | Ile | Ile | Glu | Arg | Asn | Lys | Thr | Glu | |
| 50 | | | | | 55 | | | | | 60 | | | | | | |

| att | gtg | tat | ctg | acc | aac | acc | act | gta | gag | aag | gaa | ata | tgc | ccc | aaa | 240 |
|---|---|---|---|---|---|---|---|---|---|---|---|---|---|---|---|---|
| Ile | Val | Tyr | Leu | Thr | Asn | Thr | Thr | Val | Glu | Lys | Glu | Ile | Cys | Pro | Lys | |
| 65 | | | | 70 | | | | | 75 | | | | | 80 | | |

| tca | aca | gaa | tac | aga | aat | tgg | tca | aag | cct | caa | tgt | aac | att | aca | gga | 288 |
|---|---|---|---|---|---|---|---|---|---|---|---|---|---|---|---|---|
| Ser | Thr | Glu | Tyr | Arg | Asn | Trp | Ser | Lys | Pro | Gln | Cys | Asn | Ile | Thr | Gly | |
| | | | | 85 | | | | | 90 | | | | | 95 | | |

| ttt | gca | cct | ttt | tct | aag | gac | aat | tcg | att | cgg | ctt | tct | gct | ggt | ggg | 336 |
|---|---|---|---|---|---|---|---|---|---|---|---|---|---|---|---|---|
| Phe | Ala | Pro | Phe | Ser | Lys | Asp | Asn | Ser | Ile | Arg | Leu | Ser | Ala | Gly | Gly | |
| | | | 100 | | | | | 105 | | | | | 110 | | | |

| gac | atc | tgg | gtg | aca | aga | gaa | cct | tat | gtg | tca | tgc | gat | cac | gac | aag | 384 |
|---|---|---|---|---|---|---|---|---|---|---|---|---|---|---|---|---|
| Asp | Ile | Trp | Val | Thr | Arg | Glu | Pro | Tyr | Val | Ser | Cys | Asp | His | Asp | Lys | |
| | | 115 | | | | | 120 | | | | | 125 | | | | |

| tgt | tat | caa | ttt | gcc | ctt | ggg | cag | gga | aca | aca | cta | aac | aac | ggg | cat | 432 |
|---|---|---|---|---|---|---|---|---|---|---|---|---|---|---|---|---|
| Cys | Tyr | Gln | Phe | Ala | Leu | Gly | Gln | Gly | Thr | Thr | Leu | Asn | Asn | Gly | His | |
| 130 | | | | | 135 | | | | | 140 | | | | | | |

| tca | aat | gac | act | gta | cat | gat | agg | acc | cct | tac | cga | acc | cta | ttg | atg | 480 |
|---|---|---|---|---|---|---|---|---|---|---|---|---|---|---|---|---|
| Ser | Asn | Asp | Thr | Val | His | Asp | Arg | Thr | Pro | Tyr | Arg | Thr | Leu | Leu | Met | |
| 145 | | | | 150 | | | | | 155 | | | | | 160 | | |

| aat | gaa | ttg | ggg | gtt | cca | ttt | cat | ttg | gga | acc | agg | caa | gtg | tgc | ata | 528 |
|---|---|---|---|---|---|---|---|---|---|---|---|---|---|---|---|---|
| Asn | Glu | Leu | Gly | Val | Pro | Phe | His | Leu | Gly | Thr | Arg | Gln | Val | Cys | Ile | |
| | | | 165 | | | | | 170 | | | | | 175 | | | |

| gca | tgg | tcc | agt | tca | agt | tgt | cac | gat | ggg | aaa | gca | tgg | ctg | cat | gtt | 576 |
|---|---|---|---|---|---|---|---|---|---|---|---|---|---|---|---|---|
| Ala | Trp | Ser | Ser | Ser | Ser | Cys | His | Asp | Gly | Lys | Ala | Trp | Leu | His | Val | |
| | | | 180 | | | | | 185 | | | | | 190 | | | |

| tgt | ata | act | ggg | gat | gat | gaa | aat | gca | act | gct | agc | ttc | att | tac | aat | 624 |
|---|---|---|---|---|---|---|---|---|---|---|---|---|---|---|---|---|
| Cys | Ile | Thr | Gly | Asp | Asp | Glu | Asn | Ala | Thr | Ala | Ser | Phe | Ile | Tyr | Asn | |
| | | 195 | | | | | 200 | | | | | 205 | | | | |

| ggg | agg | cta | gta | gat | agt | att | ggt | tca | tgg | tcc | aaa | aat | ata | cta | aga | 672 |
|---|---|---|---|---|---|---|---|---|---|---|---|---|---|---|---|---|
| Gly | Arg | Leu | Val | Asp | Ser | Ile | Gly | Ser | Trp | Ser | Lys | Asn | Ile | Leu | Arg | |
| | 210 | | | | | 215 | | | | | 220 | | | | | |

| acc | cag | gag | tcg | gaa | tgc | gtt | tgt | att | aat | gga | act | tgt | aca | gta | gtc | 720 |
|---|---|---|---|---|---|---|---|---|---|---|---|---|---|---|---|---|
| Thr | Gln | Glu | Ser | Glu | Cys | Val | Cys | Ile | Asn | Gly | Thr | Cys | Thr | Val | Val | |
| 225 | | | | | 230 | | | | | 235 | | | | | 240 | |

| atg | act | gat | gga | agc | gct | tcc | gga | aaa | gct | gat | act | aaa | ata | tta | ttc | 768 |
|---|---|---|---|---|---|---|---|---|---|---|---|---|---|---|---|---|
| Met | Thr | Asp | Gly | Ser | Ala | Ser | Gly | Lys | Ala | Asp | Thr | Lys | Ile | Leu | Phe | |
| | | | | 245 | | | | | 250 | | | | | 255 | | |

| att | gag | gag | ggg | aaa | atc | att | cat | att | agc | acg | ttg | tca | gga | agt | gcg | 816 |
|---|---|---|---|---|---|---|---|---|---|---|---|---|---|---|---|---|
| Ile | Glu | Glu | Gly | Lys | Ile | Ile | His | Ile | Ser | Thr | Leu | Ser | Gly | Ser | Ala | |
| | | | 260 | | | | | 265 | | | | | 270 | | | |

| cag | cac | gta | gag | gag | tgc | tct | tgt | tat | cct | cga | tat | cct | ggt | gtc | aga | 864 |
|---|---|---|---|---|---|---|---|---|---|---|---|---|---|---|---|---|
| Gln | His | Val | Glu | Glu | Cys | Ser | Cys | Tyr | Pro | Arg | Tyr | Pro | Gly | Val | Arg | |
| | | 275 | | | | | 280 | | | | | 285 | | | | |

| tgt | gtc | tgc | aga | gac | aac | tgg | aaa | ggc | tcc | aat | agg | ccc | ata | gtt | gat | 912 |
|---|---|---|---|---|---|---|---|---|---|---|---|---|---|---|---|---|
| Cys | Val | Cys | Arg | Asp | Asn | Trp | Lys | Gly | Ser | Asn | Arg | Pro | Ile | Val | Asp | |
| | 290 | | | | | 295 | | | | | 300 | | | | | |

-continued

| | | | | | | | | | | | | | | | | |
|---|---|---|---|---|---|---|---|---|---|---|---|---|---|---|---|---|
| ata | aat | gta | aag | gat | tat | agc | act | gtt | tcc | agt | tat | gta | tgc | tct | gga | 960 |
| Ile | Asn | Val | Lys | Asp | Tyr | Ser | Thr | Val | Ser | Ser | Tyr | Val | Cys | Ser | Gly | |
| 305 | | | | 310 | | | | 315 | | | | 320 | | | | |
| ctt | gtt | gga | gac | aca | ccc | aga | aaa | aac | gac | agc | ttc | agc | agt | agt | aat | 1008 |
| Leu | Val | Gly | Asp | Thr | Pro | Arg | Lys | Asn | Asp | Ser | Phe | Ser | Ser | Ser | Asn | |
| | | | 325 | | | | | 330 | | | | | 335 | | | |
| tgc | cta | gac | cct | aat | aat | gag | gaa | ggt | ggt | cat | ggg | gta | aaa | ggt | tgg | 1056 |
| Cys | Leu | Asp | Pro | Asn | Asn | Glu | Glu | Gly | Gly | His | Gly | Val | Lys | Gly | Trp | |
| | | | 340 | | | | | 345 | | | | | 350 | | | |
| gcc | ttt | gat | gat | gga | gat | gac | ttg | tgg | atg | gga | aga | acg | atc | agc | gag | 1104 |
| Ala | Phe | Asp | Asp | Gly | Asp | Asp | Leu | Trp | Met | Gly | Arg | Thr | Ile | Ser | Glu | |
| | | | 355 | | | | | 360 | | | | | 365 | | | |
| aag | tca | cgt | tta | ggc | tat | gaa | acc | ttc | aaa | gtc | gtc | aaa | gga | tgg | tcc | 1152 |
| Lys | Ser | Arg | Leu | Gly | Tyr | Glu | Thr | Phe | Lys | Val | Val | Lys | Gly | Trp | Ser | |
| | 370 | | | | | 375 | | | | | 380 | | | | | |
| aaa | ccc | aac | tcc | aaa | tta | cag | aca | aat | agg | caa | gtt | ata | gtt | gat | aga | 1200 |
| Lys | Pro | Asn | Ser | Lys | Leu | Gln | Thr | Asn | Arg | Gln | Val | Ile | Val | Asp | Arg | |
| 385 | | | | | 390 | | | | | 395 | | | | | 400 | |
| ggt | aac | agg | tcc | ggt | tat | tct | ggt | att | ttc | tcc | att | gaa | ggc | aaa | aac | 1248 |
| Gly | Asn | Arg | Ser | Gly | Tyr | Ser | Gly | Ile | Phe | Ser | Ile | Glu | Gly | Lys | Asn | |
| | | | | 405 | | | | | 410 | | | | | 415 | | |
| tgt | att | aat | agg | tgc | ttt | tat | gtg | gag | ttg | ata | agg | gga | agg | aaa | gag | 1296 |
| Cys | Ile | Asn | Arg | Cys | Phe | Tyr | Val | Glu | Leu | Ile | Arg | Gly | Arg | Lys | Glu | |
| | | | 420 | | | | | 425 | | | | | 430 | | | |
| gaa | act | aaa | gtc | ttg | tgg | acc | tca | aac | agt | att | gtt | gtg | ttt | tgt | ggc | 1344 |
| Glu | Thr | Lys | Val | Leu | Trp | Thr | Ser | Asn | Ser | Ile | Val | Val | Phe | Cys | Gly | |
| | | | 435 | | | | | 440 | | | | | 445 | | | |
| acc | tca | ggt | acg | tat | gga | aca | ggc | tca | tgg | cct | gat | ggg | gcg | gat | atc | 1392 |
| Thr | Ser | Gly | Thr | Tyr | Gly | Thr | Gly | Ser | Trp | Pro | Asp | Gly | Ala | Asp | Ile | |
| | | | 450 | | | | | 455 | | | | | 460 | | | |
| aat | ctc | atg | cct | ata | taa | | | | | | | | | | | 1410 |
| Asn | Leu | Met | Pro | Ile | | | | | | | | | | | | |
| 465 | | | | | | | | | | | | | | | | |

```
<210> SEQ ID NO 4
<211> LENGTH: 469
<212> TYPE: PRT
<213> ORGANISM: Influenza A virus
<220> FEATURE:
<221> NAME/KEY: MISC_FEATURE
<222> LOCATION: (1)..(469)
<223> OTHER INFORMATION: expressed N2 subtype

<400> SEQUENCE: 4
```

Met Asn Pro Asn Gln Lys Ile Ile Thr Ile Gly Ser Val Ser Leu Ile
1               5                   10                  15

Ile Ala Thr Ile Cys Phe Leu Met Gln Ile Ala Ile Leu Val Thr Thr
                20                  25                  30

Val Thr Leu His Phe Lys Gln His Asn Cys Asp Ser Ser Pro Asn Asn
            35                  40                  45

His Val Met Phe Cys Glu Pro Thr Ile Ile Glu Arg Asn Lys Thr Glu
        50                  55                  60

Ile Val Tyr Leu Thr Asn Thr Val Glu Lys Glu Ile Cys Pro Lys
65                  70                  75                  80

Ser Thr Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp His Asp Lys
        115                 120                 125

Cys Tyr Gln Phe Ala Leu Gly Gln Gly Thr Thr Leu Asn Asn Gly His
                130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Arg Gln Val Cys Ile
                165                 170                 175

Ala Trp Ser Ser Ser Cys His Asp Gly Lys Ala Trp Leu His Val
                180                 185                 190

Cys Ile Thr Gly Asp Asp Glu Asn Ala Thr Ala Ser Phe Ile Tyr Asn
            195                 200                 205

Gly Arg Leu Val Asp Ser Ile Gly Ser Trp Ser Lys Asn Ile Leu Arg
            210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Ile His Ile Ser Thr Leu Ser Gly Ser Ala
                260                 265                 270

Gln His Val Glu Glu Cys Ser Cys Tyr Pro Arg Tyr Pro Gly Val Arg
            275                 280                 285

Cys Val Cys Arg Asp Asn Trp Lys Gly Ser Asn Arg Pro Ile Val Asp
290                 295                 300

Ile Asn Val Lys Asp Tyr Ser Thr Val Ser Ser Tyr Val Cys Ser Gly
305                 310                 315                 320

Leu Val Gly Asp Thr Pro Arg Lys Asn Asp Ser Phe Ser Ser Ser Asn
                325                 330                 335

Cys Leu Asp Pro Asn Asn Glu Glu Gly Gly His Gly Val Lys Gly Trp
            340                 345                 350

Ala Phe Asp Asp Gly Asp Asp Leu Trp Met Gly Arg Thr Ile Ser Glu
            355                 360                 365

Lys Ser Arg Leu Gly Tyr Glu Thr Phe Lys Val Val Lys Gly Trp Ser
            370                 375                 380

Lys Pro Asn Ser Lys Leu Gln Thr Asn Arg Gln Val Ile Val Asp Arg
385                 390                 395                 400

Gly Asn Arg Ser Gly Tyr Ser Gly Ile Phe Ser Ile Glu Gly Lys Asn
                405                 410                 415

Cys Ile Asn Arg Cys Phe Tyr Val Glu Leu Ile Arg Gly Arg Lys Glu
            420                 425                 430

Glu Thr Lys Val Leu Trp Thr Ser Asn Ser Ile Val Val Phe Cys Gly
            435                 440                 445

Thr Ser Gly Thr Tyr Gly Thr Gly Ser Trp Pro Asp Gly Ala Asp Ile
            450                 455                 460

Asn Leu Met Pro Ile
465

<210> SEQ ID NO 5
<211> LENGTH: 478
<212> TYPE: PRT
<213> ORGANISM: Artificial Sequence
<220> FEATURE:
<223> OTHER INFORMATION: Recombinant expressed protein of NA1 containing
      baculovirus GP67 and His tag

<400> SEQUENCE: 5

Met Leu Leu Val Asn Gln Ser His Gln Gly Phe Asn Lys Glu His Thr

```
1               5                   10                  15
Ser Lys Met Val Ser Ala Ile Val Leu Tyr Val Leu Ala Ala Ala
            20                  25                  30

Ala His Ser Ala Phe Ala His Ser Ile Gln Thr Gly Trp Glu Asn His
            35                  40                  45

Thr Gly Met Cys Asn Gln Ser Val Ile Thr Tyr Val Asn Asn Thr Trp
            50                  55                  60

Val Asn Arg Thr Tyr Val Asn Ile Ser Asn Ile Lys Ile Ala Thr Ile
65                  70                  75                  80

Gln Asp Val Thr Pro Ile Ile Leu Ala Gly Asn Ser Pro Leu Cys Pro
                85                  90                  95

Val Ser Gly Trp Ala Val Tyr Ser Lys Asp Asn Ser Ile Arg Ile Gly
                100                 105                 110

Ser Lys Gly Asp Ile Phe Val Ile Arg Glu Pro Phe Ile Ser Cys Ser
            115                 120                 125

Gln Leu Glu Cys Arg Thr Phe Phe Leu Thr Gln Gly Ala Leu Leu Asn
            130                 135                 140

Asp Lys His Ser Asn Gly Thr Val Lys Asp Arg Ser Pro Tyr Arg Thr
145                 150                 155                 160

Leu Met Ser Cys Pro Ile Gly Glu Ala Pro Ser Pro Tyr Asn Ser Arg
                165                 170                 175

Phe Glu Ser Val Ala Trp Ser Ala Ser Ala Cys His Asp Gly Met Gly
                180                 185                 190

Trp Leu Thr Ile Gly Val Ser Gly Pro Asp Asn Gly Ala Val Ala Val
            195                 200                 205

Leu Lys Tyr Asn Gly Ile Ile Thr Asp Thr Ile Lys Ser Trp Arg Asn
    210                 215                 220

Lys Ile Leu Arg Thr Gln Glu Ser Glu Cys Val Cys Met Asn Gly Ser
225                 230                 235                 240

Cys Phe Thr Val Leu Thr Asp Gly Pro Ser Asn Gly Gln Ala Ser Tyr
                245                 250                 255

Lys Ile Phe Lys Val Glu Lys Gly Lys Ile Ile Lys Ser Ile Glu Leu
                260                 265                 270

Asp Ala Pro Asn Tyr His Tyr Glu Glu Cys Ser Cys Tyr Pro Asp Thr
            275                 280                 285

Gly Lys Val Met Cys Val Cys Arg Asp Asn Trp His Ala Ser Asn Arg
            290                 295                 300

Pro Trp Val Ser Phe Asn Gln Asn Leu Asp Tyr Gln Ile Gly Tyr Ile
305                 310                 315                 320

Cys Ser Gly Val Phe Gly Asp Asn Pro Arg Ser Thr Asp Gly Lys Gly
                325                 330                 335

Asn Cys Gly Pro Val Leu Ser Asn Gly Ala Asn Gly Val Lys Gly Phe
            340                 345                 350

Ser Tyr Arg Tyr Gly Asn Gly Val Trp Ile Gly Arg Thr Lys Ser Ile
            355                 360                 365

Asn Ser Arg Ser Gly Phe Glu Met Ile Trp Asp Pro Asn Gly Trp Thr
    370                 375                 380

Glu Thr Asp Ser Ser Phe Ser Met Lys Gln Asp Ile Ile Ala Leu Asp
385                 390                 395                 400

Asp Trp Ser Gly Tyr Ser Gly Ser Phe Val Gln His Pro Glu Leu Thr
                405                 410                 415

Gly Met Asn Cys Ile Arg Pro Cys Phe Trp Val Glu Leu Ile Arg Gly
                420                 425                 430
```

```
Gln Pro Lys Glu Ser Thr Ile Trp Ala Ser Gly Ser Ile Ser Phe
        435                 440                 445

Cys Gly Val Asn Ser Glu Thr Ala Asn Trp Ser Trp Pro Asp Gly Ala
    450                 455                 460

Ile Leu Pro Phe Ala Ile Asp Lys His His His His His His
465                 470                 475
```

<210> SEQ ID NO 6
<211> LENGTH: 478
<212> TYPE: PRT
<213> ORGANISM: Artificial Sequence
<220> FEATURE:
<223> OTHER INFORMATION: Recombinant expressed protein of NA2 containing baculovirus GP67 and His tag

<400> SEQUENCE: 6

```
Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala His Phe Lys Gln His Asn Cys Asp Ser Ser
        35                  40                  45

Pro Asn Asn His Val Met Phe Cys Glu Pro Thr Ile Ile Glu Arg Asn
    50                  55                  60

Lys Thr Glu Ile Val Tyr Leu Thr Asn Thr Thr Val Glu Lys Glu Ile
65                  70                  75                  80

Cys Pro Lys Ser Thr Glu Tyr Arg Asn Trp Ser Lys Pro Gln Cys Asn
                85                  90                  95

Ile Thr Gly Phe Ala Pro Phe Ser Lys Asp Asn Ser Ile Arg Leu Ser
            100                 105                 110

Ala Gly Gly Asp Ile Trp Val Thr Arg Glu Pro Tyr Val Ser Cys Asp
        115                 120                 125

His Asp Lys Cys Tyr Gln Phe Ala Leu Gly Gln Gly Thr Thr Leu Asn
    130                 135                 140

Asn Gly His Ser Asn Asp Thr Val His Asp Arg Thr Pro Tyr Arg Thr
145                 150                 155                 160

Leu Leu Met Asn Glu Leu Gly Val Pro Phe His Leu Gly Thr Arg Gln
                165                 170                 175

Val Cys Ile Ala Trp Ser Ser Ser Cys His Asp Gly Lys Ala Trp
            180                 185                 190

Leu His Val Cys Ile Thr Gly Asp Asp Glu Asn Ala Thr Ala Ser Phe
        195                 200                 205

Ile Tyr Asn Gly Arg Leu Val Asp Ser Ile Gly Ser Trp Ser Lys Asn
    210                 215                 220

Ile Leu Arg Thr Gln Glu Ser Glu Cys Val Cys Ile Asn Gly Thr Cys
225                 230                 235                 240

Thr Val Val Met Thr Asp Gly Ser Ala Ser Gly Lys Ala Asp Thr Lys
                245                 250                 255

Ile Leu Phe Ile Glu Glu Gly Lys Ile Ile His Ile Ser Thr Leu Ser
            260                 265                 270

Gly Ser Ala Gln His Val Glu Glu Cys Ser Cys Tyr Pro Arg Tyr Pro
        275                 280                 285

Gly Val Arg Cys Val Cys Arg Asp Asn Trp Lys Gly Ser Asn Arg Pro
    290                 295                 300

Ile Val Asp Ile Asn Val Lys Asp Tyr Ser Thr Val Ser Ser Tyr Val
```

```
                305                 310                 315                 320
Cys Ser Gly Leu Val Gly Asp Thr Pro Arg Lys Asn Asp Ser Phe Ser
                    325                 330                 335

Ser Ser Asn Cys Leu Asp Pro Asn Asn Glu Glu Gly Gly His Gly Val
                340                 345                 350

Lys Gly Trp Ala Phe Asp Asp Gly Asp Asp Leu Trp Met Gly Arg Thr
            355                 360                 365

Ile Ser Glu Lys Ser Arg Leu Gly Tyr Glu Thr Phe Lys Val Val Lys
        370                 375                 380

Gly Trp Ser Lys Pro Asn Ser Lys Leu Gln Thr Asn Arg Gln Val Ile
385                 390                 395                 400

Val Asp Arg Gly Asn Arg Ser Gly Tyr Ser Gly Ile Phe Ser Ile Glu
                405                 410                 415

Gly Lys Asn Cys Ile Asn Arg Cys Phe Tyr Val Glu Leu Ile Arg Gly
                420                 425                 430

Arg Lys Glu Glu Thr Lys Val Leu Trp Thr Ser Asn Ser Ile Val Val
                435                 440                 445

Phe Cys Gly Thr Ser Gly Thr Tyr Gly Thr Gly Ser Trp Pro Asp Gly
        450                 455                 460

Ala Asp Ile Asn Leu Met Pro Ile His His His His His His
465                 470                 475
```

UNIVERSAL INFLUENZA VACCINE

CROSS-REFERENCE TO RELATED APPLICATIONS

The present application claims the priority benefit of U.S. Provisional Patent Application Ser. No. 62/778,409, filed Dec. 12, 2018, entitled UNIVERSAL INFLUENZA VACCINE, incorporated by reference in its entirety herein.

SEQUENCE LISTING

The following application contains a sequence listing in computer readable format (CRF), submitted as a text file in ASCII format entitled "SequenceListing," created on Nov. 5, 2019, as 40 KB. The content of the CRF is hereby incorporated by reference.

BACKGROUND

Field of the Invention

The present disclosure relates to vaccines against influenza, and particularly influenza A, which elicit anti-neuraminidase antibodies.

Description of Related Art

Swine influenza (SI) is an acute respiratory disease caused by influenza A viruses, which is an enveloped virus of the Orthomyxoviridae family. Swine influenza virus (SIV) is both a pathogen of economic significance to the swine industry. An additional concern regarding SIV is its zoonotic potential as under certain circumstances it can be transmitted to humans, which is best exemplified by the 2009 H1N1 pandemic originated from a swine source. For that reason, it is a high priority agent in animal health for the USDA.

A typical outbreak of respiratory disease caused by SIV is characterized by sudden onset and rapid spread within a herd. Clinical symptoms associated with SI may include coughing, sneezing, nasal discharge, elevated rectal temperature, lethargy, breathing difficulty, and depressed appetite. While morbidity rates may reach 100% with SIV infections, mortality rates are generally low.

The genome of SIV is separated into 8 independent RNA segments that allows for frequent reassortment when two different viruses infect and replicate within the same cell of a pig. Reassortment often results in the production of a new influenza virus (antigenic shift), which renders the current strain-specific vaccine strategy ineffective. In addition, influenza A virus has the unique capacity to undergo genetic variations (antigenic drift) in that it can mutate up to 50% of the amino acid sequence of its major surface protein, hemagglutinin (HA), without changing the function of the HA protein. Antigenic drift and antigenic shift contribute to apparent failures of SI vaccines when used in the swine industry.

In the USA, H1N1, H1N2 and H3N2 subtypes are the major causes of SI outbreaks, although other subtypes have been isolated from diseased pigs. Each subtype also consists of several genetic and antigenic clusters. The contemporary H3N2 SIV strain is a triple reassortant strain, resulting from contributions of human, avian, and SI viral lineages. H3N2 is widely spread in U.S. swine herds. A similar reassortant mechanism resulted in the emergence and rapid spread of a triple reassortant H1N1 virus that has also become endemic in U.S. swine populations.

Currently available SI vaccines are based on killed viruses containing H1N1, H1N2 and H3N2 subtypes. Due to antigenic drift and shift, the killed vaccines are very limited in offering protection against SIV strains genetically and antigenically different from the vaccine strains. These killed vaccines appear also to be associated with disease enhancement in vaccinated pigs under some circumstances after virus infection.

Nevertheless, vaccination remains the most effective approach to prevent influenza epidemics. Conventional influenza vaccines can prevent clinical disease, but their efficacy depends on the extent of antigenic "match" between the strains used for vaccine preparation and those circulating in the population. This challenge has focused numerous efforts towards discovering a vaccine candidate that elicits a broad-spectrum protection against diverse influenza subtypes, also termed a universal vaccine.

Influenza A virus has two large surface glycoproteins, HA and neuraminidase (NA). The HA mediates the viral receptor binding and entry process, while the NA catalytically drives the release of newly formed virus particles as well as promotes the movement of virus particles via mucosal surfaces.

While several commercial inactivated whole-virus, as well as autogenous vaccines, are widely used, efficacy in field conditions is often lacking due to genetic mismatch between vaccine strains and challenge virus. The immune response following vaccination is largely humoral and directed almost exclusively against the immunodominant HA gene. While antibodies recognizing the HA are often neutralizing and can confer sterilizing immunity, mismatch between antibodies and virus can lead to a loss of binding or even enhancement of disease, a phenomenon referred to vaccination associated-enhancement of respiratory disease (VAERD).

Numerous studies have shown that NA-specific antibodies are effective in offering protection from influenza by blocking viral particle release. NA as an important target for control, and prevention of influenza A virus infection has been demonstrated by FDA-approved therapeutic antiviral drugs like Oseltamivir and Zanamivir (NA inhibitors). The viral NA differs from viral HA in that the NA protein is relatively more conserved than HA among different influenza strains and swine and human isolates principally consist of two major subtypes, termed N1 and N2. Currently marketed influenza vaccines contain an NA component (among other viral particles) but are generally incapable of inducing protective anti-NA antibodies largely due to the immunodominance of the viral HA protein that is also contained in such vaccines. Despite being a viral surface glycoprotein like HA, the natural immune response directed towards NA is substantially less than that of HA. As a consequence, NA exhibits less variability than HA and represents a more conserved antigen. More prominent presentation of NA to the immune system, either by dissociation of the virion or by recombinant expression of NA, has been shown to elicit a stronger anti-NA antibody response.

Both the HA and NA proteins are critical to the influenza virus life cycle. HA allows the virus to bind to cell surface sialic acids present on cellular membrane proteins, leading to endocytosis and virus internalization. In contrast, NA cleaves sialic acids from the host cell allowing mature virions to release and disseminate. While HA antibodies can ideally prevent infection, NA antibodies allow cell infection but prevent virus dissemination. This allows for a more robust immune response as antigen can be processed via both MHCI and MHCII, effectively stimulating infection immunity.

The baculovirus expression system is widely used for vaccine production. Examples in humans include vaccines for human papillomavirus and influenza virus, while in pigs baculovirus is used for numerous porcine circovirus type 2 vaccines. Baculovirus expression is popular for vaccine antigen production owing to several features. Baculoviruses can only infect certain insects, making them extremely safe for use in mammals. Large amounts of antigen can also easily be produced using baculovirus expression systems, making them economical.

SUMMARY OF INVENTION

Immunogenic compositions for inducing a universal immune response to influenza. The composition comprises recombinant baculovirus expression vectors in cultured insect cells dispersed in a pharmaceutically-acceptable carrier comprising insect cell culture media and optional adjuvant. The recombinant baculovirus expression vectors express NA. Preferably, the NA is a recombinantly-expressed wild-type NA protein.

Kits for stimulating a universal immune response against influenza infection are also described. The kits comprise an immunogenic composition according to any one of the embodiments described herein and instructions for administering the composition to a host animal susceptible to influenza.

Also described herein are methods of stimulating a universal immune response against influenza infection. The methods comprise administering an immunogenic composition according to any one of the embodiments described herein to a host animal susceptible to influenza in an effective amount. Advantageously, the immunogenic compositions provide a "universal" immune response in that the anti-NA antibodies stimulated by the vaccine provide protection against heterologous influenza infections (i.e., infections from other strains which are different from the strain from which the recombinantly-expressed NA is derived).

DETAILED DESCRIPTION

Figure 1:
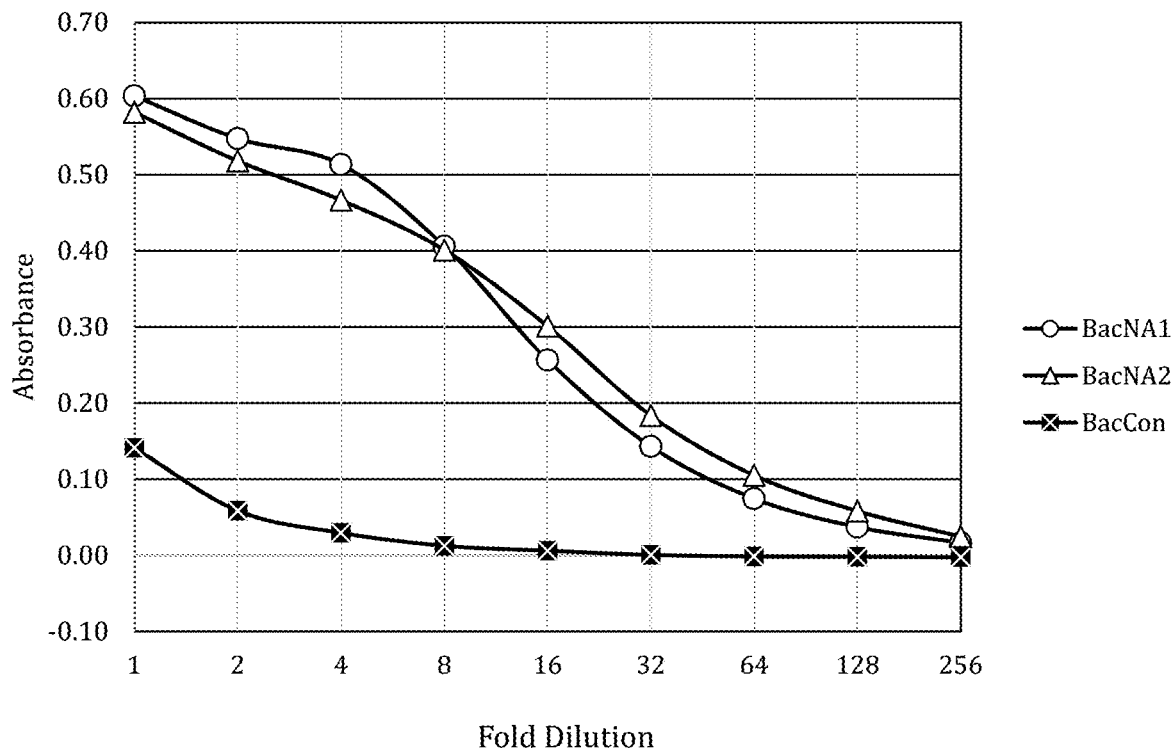
FIG. 1 is a graph demonstrating activity of NA expressed in the recombinant baculovirus expression system.

Our universal influenza vaccine strategy is to develop a recombinantly-expressed neuraminidase-based protective vaccine for influenza virus, such as against SI, produced in a baculovirus expression system. Baculovirus expression systems and baculovirus expression vectors in general have been described extensively in the literature, including U.S. Pat. No. 4,745,051, O'Reilly at al. (Baculovirus Expression Vectors, A Laboratory Manual. (1993)), and Murhammer (Baculovirus and Insect Cell Expression Protocols. In: Methods in Molecular Biology™. Volume 388 (2007)), incorporated by reference herein.

Immunogenic compositions are described herein which comprise recombinant baculovirus expression vectors in cultured insect cells dispersed in cell culture media, along with an optional adjuvant (oil-in-water, water-in-oil, etc.). The baculovirus expression vectors direct the expression of native or wild-type NA proteins in the infected insect cells. That is, unlike previous approaches using modified NA proteins, such as those in which the transmembrane domain has been modified or deleted, the present expression systems are engineered in a way that the full-length, wild-type or native NA protein sequence is expressed in the system (and not a truncated version), and more particularly the native or wild-type NA protein is expressed as part of the insect cell membrane proteins, and can be found integrated into the insect cell membranes, as well as in the budded baculovirus membranes in the culture supernatants. Preferably, the full-length, wild-type/native NA coding sequence (cDNA) is cloned into the baculovirus system for expression. It will be appreciated that such sequences can be identified based upon the circulating strains isolated in a population at a given time, and synthesized to create updated vaccines targeted to circulating strains. However, as shown in the data, the inventive vaccines provide protection against heterologous challenge. Therefore, protective immunity may be obtained even from vaccines different from the circulating strains. Advantageously, since the expression systems are engineered to express the full-length, wild-type/native NA protein, which is associated with and presented by membrane components in the expression system (i.e., the infected insect cells and the baculoviral components), and not as free, soluble recombinant NA in solution, it is believed that the expressed NA protein in the inventive vaccine is presented to the immune system in a manner (folded structure) more closely resembling (and perhaps substantially similar to) its native conformation, further enhancing the immune response.

Crude and unpurified cultures of the expression system components are preferably used for the immunogenic compositions, that is, as a crude cell culture containing the unpurified infected cells (presenting NA), baculovirus (expressing NA), and cell media, along with optional adjuvant. In other words, the infected cell culture may be chemically inactivated, but is not otherwise processed or purified.

Exemplary insect cells for use in the invention include Lepidopteran species *Spodoptera frugiperda* and cell lines derived therefrom. Other insect cell hosts can be used including *Trichoplusia ni, Bombyx mori*, cell lines derived therefrom, and the like. Particularly preferred insect cell lines include SF9 (and variants), SF21, High Five (BTI-TN-5B1-4), and the like. Any suitable culture media can be used to propagate the cells. Culture media suitable for insect cell culture is preferably serum-free, and various formulations are known in the art and widely available, such as SF900II. In general, the culture medium will comprise a mixture of amino acids, sugars, salts, proteins, and the like. Publicly available formulations such as Grace's media are also suitable. Various baculovirus expression systems are commercially available. Exemplary baculovirus expression vectors will generally include ProEasy (AB Vector), BaculoGold™ DNA (PharMingen), Bac-N-Blue™ DNA (Invitrogen), or BacPAK6™ DNA (Clontech) for co-transfection with the transfer vector (donor or shuttle) plasmid DNA containing the foreign gene. Alternatively, insect cells are transfected with a recombinant bacmid DNA constructed by transposition of the donor plasmid DNA in *E. coli* cells, using the Bac-to-Bac™ (Invitrogen-Gibco/Life Technologies) system. Multiple gene transfer vectors, such as pAcAB3 and pAcAB4 are particularly preferred.

Favorable baculovirus expression vectors utilize double recombination between the multiple gene transfer vector and baculovirus genomic DNA which is linearized by Bsu36.I such that a portion of the essential gene ORF1629 is lost due to genomic DNA digestion. Double recombination between the transfer vector and the linearized baculovirus DNA restores ORF1629 and concurrently mediates integration of the heterologous gene expression cassette into the baculovirus genome. A further favorable feature of this system is the utilization of baculovirus genomic DNA derived from a baculovirus strain carrying a conditionally-lethal gene which is lost via linearization with Bsu36.I. This feature ensures that any contaminating uncut parental baculovirus DNA does not lead to rescue of parental virus, ensuring that all rescued baculoviruses are derived from recombination with the transfer vector.

The various components of the immunogenic composition will be selected to be pharmaceutically acceptable. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained. A pharmaceutically-acceptable carrier would naturally be selected to minimize any degradation of the baculovirus, insect cells, and other components and to minimize any adverse side effects in the subject, as would be well known to one of skill in the art. Pharmaceutically-acceptable ingredients include those acceptable for veterinary use as well as human pharmaceutical use, and will depend on the route of administration.

Native/wild-type NA proteins are recombinantly expressed at high levels in the insect cells infected with the baculovirus expression vectors. Advantageously, the primary gene product is unprocessed, full length NA which remains associated with the cell membrane of infected insect cells, as well as budded baculovirus membranes. As such, unlike purified or soluble forms of NA, such as those which have been modified or mutated, the NA in the inventive compositions is presented on the surface of such membranes and complexes, likely contributing to the immunogenicity of the composition (particularly as displayed on the baculovirus viral membrane surface) as discussed herein.

Expression plasmids can be generated using sequence information for NA, based upon publicly available sequences and/or based upon newly sequenced circulating strains. Exemplary NA sequences include Genbank accessions KY115564 and KU752376, or conservatively modified variants thereof that retain the functionality of NA, or sequences which encode for NA protein, such as Genbank accessions APG56794.1 and AMP44884.1, or conservatively modified variants thereof that retain the functionality of NA. It will be appreciated that wild-type/native NA sequences for use as vaccines in various species can be identified from publicly available sequences and/or from circulating strains, such that up-to-date vaccines can be developed. The identified sequences are synthesized into cDNA and inserted or cloned into the baculovirus expression vectors along with appropriate control sequences, promoters, etc. The resulting expression vectors can then be transfected into appropriate insect cells, and the crude culture can be used for vaccine production.

Ideally, the immunogenic compositions will include a mixture of two or more NA protein subtypes to provide multi-valent protection. However, this will also depend on the species to be vaccinated. For example, pigs are known to be infected with both N1 and N2 strains. However, dogs are more likely to be infected with only N2. Thus, for certain species, only one NA protein subtype may be necessary to achieve vaccination. The platform developed is exemplified in pigs in the working examples, where we have developed the BacNA1 expression construct that was used in our studies. NA1 (SEQ ID NO:2) is derived from A/swine/Iowa/A01782229/2016 H1N1 (SEQ ID NO:1). We also generated a BacNA2 expression plasmid derived from A/swine/Oklahoma/A01730659/2016 H1N2 (SEQ ID NO:3). As noted above, suitable baculovirus expression shuttle vectors, such as pAcAB3, are commercially available. However, it will be appreciated that the vaccine platform can be applied to a variety of other species susceptible to influenza infection, including poultry, canines, equines, and felines, as well as humans.

In one or more embodiments concerned with research and study, a baculovirus secretion signal sequence (e.g., GP67) and affinity tag (e.g., polyhistidine-tag) can be added to the NA gene during synthesis to facilitate secretion of the protein into the supernatant during cell culture (which is useful for study and research of the secreted protein by affinity chromatography). Isolation and purification from culture medium for research and study is considerably easier than purification from cell lysates, as cellular material does not need to be removed from the preparation.

However, for vaccine preparation, baculoviruses expressing native NA proteins can be prepared by gently mix plasmid DNA (e.g., pAcAB3 shuttle vector containing NA1 or NA2) and linearized baculovirus DNA (purchased from ABVECTOR) followed by adding Profectin (ABVECTOR) dropwise into the mixture. After a 10-minute incubation, DNA-Profectin mixture will be added into semi-confluent monolayer of insect cells (e.g., SF9) for an additional 72-hours of incubation. Following the confirmation of NA1 and NA2 protein expression in Western-blot and NA activity assays, seed virus stocks (BacNA1 and NacNA1) can be titrated and optimized in terms of the infectious dose and culture time. The cell culture can be inactivated using an appropriate chemical treatment, such as with formaldehyde, β-propiolactone, ethylenimine, binary ethylenimine, or thimerosal (and preferably binary ethylenimine).

Preferably, the antigenic influenza components in the immunogenic compositions according to the invention consist of influenza NA-type proteins. That is, the immunogenic compositions are preferably substantially free of other influenza proteins, subunits, particles, etc., such as influenza HA, matrix proteins (M1 or M2), RNA polymerase subunits PB1, PB2, and PA, nucleoprotein (NP), nonstructural proteins (NS1, NS2), or associated virus like particles. As used here, "substantially free" means that the component is not intentionally added or part of the composition, although it is recognized that residual or incidental amounts or impurities may be present in low amounts (e.g., less than about 0.1% by weight and preferably less than about 0.01% by weight, based upon the total weight of the composite taken as 100% by weight). That is, the only influenza antigenic component(s) present in the inventive compositions is NA (and preferably mixtures of NA1 and NA2). More preferably, the recombinantly-expressed NA proteins in the vaccine are membrane-bound or membrane-associated, full-length, or native NA proteins (as opposed to free, soluble, modified NA proteins).

The immunogenic compositions can comprise a therapeutically effective amount of NA dispersed in a suitable carrier. Examples include aqueous solutions such as sterile water/distilled autoclaved water (DAW), phosphate buffered saline (PBS), normal (n.) saline (~0.9% NaCl), aqueous dextrose solutions, aqueous glycerol solutions, ethanol, normal allantoic fluid, various oil-in-water or water-in-oil emulsions, as well as dimethyl sulfoxide (DMSO) or other acceptable vehicles, and the like. In the inventive compositions suitable carriers further include cell culture media used for culturing the insect cells, and cell culture supernatants. As discussed herein, the expressed NA is preferably not purified or isolated from the expression systems and mixed with a suitable carrier to generate the inventive vaccines. Rather, the expressed NA, along with infected insect cells, membrane particles, and recombinant baculovirus (and associated cell culture and supernatants) can be directly dispersed in a carrier system noted above for administration without purification. The amount included in the composition is an amount that provides a therapeutically effective amount of expressed NA. Methods are described herein for detecting the amount of NA expressed from a given expression system.

As used herein, a "therapeutically effective" amount refers to the amount that will elicit the biological or medical response of a tissue, system, or subject that is being sought by a researcher or clinician, and in particular elicit some desired protective effect as against the viral infection by priming or stimulating an immune response specific for one or more strains of influenza virus (and preferably at least the target strain). One of skill in the art recognizes that an amount may be considered therapeutically "effective" even if the condition is not totally eradicated or prevented, but it or its symptoms and/or effects are improved or alleviated partially in the subject. In some embodiments, the composition will comprise at least about 1 μg total NA, preferably at least 5 μg total NA, more preferably at least 10 μg total NA, more preferably at least 15 μg total NA, more preferably more preferably at least 20 μg total NA, and even more preferably about 25 μg per dose or more. As used here "total" NA clarifies that if two different subtypes of NA are included in the vaccine, the total amount of all subtypes of NA in the composition.

Other ingredients may be included in the composition, such as adjuvants, other active agents, preservatives, buffering agents, salts, other pharmaceutically-acceptable ingredients. The term "adjuvant" is used herein to refer to substances that have immunopotentiating effects and are added to or co-formulated in the vaccine composition in order to enhance, elicit, and/or modulate the innate, humoral, and/or cell-mediated immune response against the vaccine components. Suitable adjuvants include: aluminum salts, such as aluminum hydroxide, aluminum phosphate, alum (potassium aluminum sulfate), or mixed aluminum salts, peptides, oil or hydrocarbon emulsions, or any other adjuvant deemed suitable for human or animal use. In one or more embodiments, the baculoviral components of the expression system itself contributes an adjuvant effect. Antibiotics can also be used as part of vaccine production and may be present in small amounts in the vaccine, such as neomycin, polymyxin B, streptomycin and gentamicin.

Advantageously, the immunogenic compositions of the invention specifically generate in the subject anti-influenza antibodies against NA only. Anti-NA antibodies do not prevent virus uptake but rather prevent the newly formed virus from escaping the cell. This is an important distinction as our vaccine also generates infection immunity, i.e., it allows a permissive infection by influenza but controls clinical disease and observable symptoms by preventing virus spread. Not only do we get immunity targeted at the antigen in the vaccine, we also stimulate cell mediated immunity by allowing the virus limited replication in the vaccinated subject.

Further, maternal anti-HA antibodies are nearly universally present in young animals, such as pigs, and interfere with vaccination. In contrast, anti-NA antibodies are largely low or non-existent in animals vaccinated with traditional vaccines or following infection. As anti-NA antibodies are low in the animals, we can vaccinate young and growing animals using the immunogenic compositions and not have maternal antibody interference.

Further, the immunogenic compositions rely on expression of full-length, wild-type/native, membrane-bound NA, which promotes a more robust immune response as compared to purified or soluble versions of NA that have been previously attempted. Again, the NA used in the present compositions is not processed or purified. Consequently, the NA is found integrated in the insect cell membranes and the budded baculovirus membranes in the culture supernatants. Presentation of NA in these complex structures likely makes it more immunogenic (especially as displayed on the baculovirus viral membrane). Measures of NA activity in the culture have shown that about half is in the cells and the other half is in the supernatant (presumably in the baculovirus membranes in the supernatant).

Homologous and heterologous challenge studies demonstrate that crude baculovirus culture (Sf9 cells+baculovirus+Sf900II media) containing at least 25 μg each of NA1 and NA2 yields protection to influenza virus. The primary measurement of protection is reduction in lung lesions. The secondary measurement of protection is reduction in influenza viral titer in the lung. Vaccination/challenge studies demonstrate the NA inhibiting antibody titers are a good correlate of protection. Vaccines formulated at a minimum of 25 μg total NA/dose yield NI titers >40, however, doses as low as 10 μg total NA have been demonstrated to provide a protective immune response.

Thus, described herein are vaccination methods or methods of stimulating an immune response against influenza infection, so as to inhibit, reduce, or even prevent symptoms of infection. The methods generally involve administering the immunogenic compositions to a host animal susceptible to influenza in an effective amount. The composition can be delivered intramuscularly, subcutaneously, intradermally, or intravenously using a needle and syringe, or a needleless injection device, as well as mucosally, such as intranasal administration. Advantageously, there have been no adverse injection site reactions observed in vaccinated subjects thus far. While stimulation of a protective immune response with a single dose is preferred, additional dosages can be administered, by the same or different route, to achieve the desired prophylactic or therapeutic effect. The vaccine can also be administered using a prime and boost regime if deemed necessary. In some embodiments, the methods described herein are useful for eliciting an immune response against influenza infection, as described above.

Advantageously, the compositions provide an immune response and heterologous protection against influenza. Ideally, the compositions include at least one NA subtype NA1 and at least one NA subtype NA2 to broaden its protection coverage. Such an "immune response" includes, for example, the production or activation of antibodies, B cells and/or the various T cells, directed specifically to NA1 and/or NA2. The immune response will be demonstrated by a lack of observable clinical symptoms, or reduction of clinical symptoms normally displayed by an infected animal, faster recovery times from infection, reduced duration or amount of viral shedding, and the like. Accordingly, vaccinated animals will display resistance to new infection (or observable signs of infection) or reduced severity of infection, as compared to unvaccinated animals. "Reducing" the incidence, severity, and/or duration of clinical symptoms and/or viral shedding, means reducing the number of infected animals in a group, reducing or eliminating the number of animals exhibiting clinical signs of infection, or reducing the severity of any clinical signs that are present in the animals, in comparison to wild-type infection in unvaccinated animals.

In some embodiments, the vaccine can be provided in unit dosage form in a suitable container. The term "unit dosage form" refers to a physically discrete unit suitable as a unitary dosage for human or animal use. Each unit dosage form may contain a predetermined amount of the vaccine (and/or other active agents) in the carrier calculated to produce the desired effect. In other embodiments, the vaccine can be provided separate from the carrier (e.g., in its own vial, ampule, sachet, or other suitable container) for on-site mixing before administration to a subject. A kit comprising the vaccine is also disclosed herein. The kit further comprises instructions for administering the vaccine to a subject. The virus can be provided as part of a dosage unit, already dispersed in a pharmaceutically-acceptable carrier (e.g., along with culture media and/or adjuvant solution), or it can be provided separately from the carrier. The kit can further comprise instructions for preparing the virus for administration to a subject, including for example, instructions for dispersing the virus in a suitable carrier.

Using the methodology and technology described herein compositions can be developed that are effective against H1N1, H3N1, H1N2, and H3N2 viruses in pigs, and can be considered "universal" vaccine candidates. In other species, NA subtypes can be sequenced and used to create compositions that provide protection against various $H_xN_1$ or $H_xN_2$ viruses. Specifically, avian influenza is typically H5N1 or H5N2. Chickens or turkeys can be vaccinated with BacNA1/BacNA2 to generate an antibody response to H5N1/H5N2 viruses. Canine influenza is typically H3N8 or H3N2 so could predict BacNA2 would protect against canine influenza. Likewise, humans are typically infected with H1N1 or H3N2 and may benefit from the vaccination strategies described herein.

As used herein, the term "vaccine" refers to an immunogenic composition capable of eliciting partial or complete immunogenic protection against a disease or condition in the subject to which it has been administered. Although vaccines are generally considered prophylactic, the vaccines may be used for therapeutic treatment of a disease or a condition. Compositions according to the embodiments disclosed herein are useful in treating viral infection from influenza in a subject (e.g., swine) and/or preventing or reducing clinical symptoms of infection. Such clinical symptoms include respiratory distress, fever, anorexia and lethargy. Thus, embodiments described herein have therapeutic and/or prophylactic uses, and in particular can be used for prophylactic treatment of a viral infection. In general, the compositions are administered prophylactically, that is, before the subject demonstrates detectable clinical signs of an infection, such that the subject develops an adaptive immune response to infection by the virus. As such, the methods are useful for preventing the development of observable clinical symptoms from viral infection, and/or reducing the incidence or severity of clinical symptoms, and/or effects of the infection, and/or reducing the duration of the infection/symptoms/effects, and/or reducing the amount and/or duration viral shedding/viremia, as compared with unvaccinated control animals. Thus, the composition may only partially prevent and/or lessen the extent of morbidity due to the viral infection (i.e., reduce the severity of the symptoms and/or effects of the infection, and/or reduce the duration of the infection/symptoms/effects), as compared with unvaccinated control animals. Yet, the composition is still considered to treat or "prevent" the target infection or disease, even though it is not 100% effective.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1: Construction of a Baculovirus Strains that Expresses SIV NA Subtype 1 (NA1) or Subtype 2 (NA2)

The synthetic NA genes were synthesized at Integrated DNA Technologies with the addition of BamHI sites immediately upstream and downstream of the gene sequence. The NA protein genes of A/swine/Iowa/A01782229/2016 (H1N1) (SEQ ID NO:1) and A/swine/Oklahoma/A01730659/2016 (H1N2) (SEQ ID NO:3) were downloaded from Genbank under accessions KY115564 and KU752376, respectively.

The synthetic NA genes were then cloned into the BamHI site of E. coli pAcAB3 (AB Vector—Catalog Number B2). After transformation into E. coli, DH5α cells, ampicillin-resistant colonies were selected and expanded in overnight 2 mL cultures of Luria-Bertani broth with 100 μg/mL ampicillin. Following plasmid DNA isolation with a Qiagen miniprep kit, plasmids were screened by restriction digestion to identify clones which contained NA1 or NA2 genes in the proper orientation (pAcAB3-NA1 and pAcAB3-NA2, respectively) by restriction endonuclease digestion. The identified clones were further verified by DNA sequencing.

Plasmid DNA (pAcAB3-NA1 and pAcAB3-NA2) along with Bsu36I-linearized baculovirus vector DNA (ProEasy, AB Vector, Catalog Number A10) were used to transfect Sf9 (Spodoptera frugiperda) insect cells to produce recombinant baculovirus encoding either the NA1 (SEQ ID NO:2) or NA2 (SEQ ID NO:4) expression cassette. Transfection was performed in a 6-well plate with $1 \times 10^6$ cells/well. For each transfection sample, plasmid DNA and Profectin Reagent (AB Vector, Catalog Number T10) complexes were prepared in 12×75 mm sterile tubes as follows:

Solution A: 45 μl water+5.0 μl Profectin transfection reagent

Solution B: 44 μl water+0.1 μg plasmid (pAcAB3-NA1 or pAcAB3-NA2)+5 μL linearized baculovirus DNA (ProEasy, AB Vector)

Solution A and Solution B were combined and incubated for 20 minutes at 20° C.+/−5° C. Then, 0.9 mL of SF-900 II medium was added to each tube before adding the complexes into SD cells. The DNA profectin complexes were transferred into Sf9 cells and incubated for 24 hrs in 27°+/−1° C. Two mL of fresh cell culture medium was then added to each well. The transfected cells were incubated at 27° C. for generation of recombinant baculovirus.

Recombinant baculoviruses produced from transfection of Sf9 cells are usually released into the medium at 4 to 5 days post-transfection. Once the cells appeared infected (cell enlargement, internal granular formation, cell detached from cell culture surface, cell degradation), the viruses were harvested from the cell culture medium by centrifugation at 500×g for 10 minutes to remove cells and large debris. The recombinant baculoviruses were called P0 viral stock.

The P1 viral stocks were amplified in Sf9 cells by inoculation of 0.5 mL of P0 material to a T75 shaker flask of ~60% confluent Sf9 cells in 20 mL of Sf900II media. P1 was harvested on day 4 post infection. Similarly, P1 harvests (1 mL) were used to infect 2-T225 flasks of Sf9 cells (~60% confluency) in 100 mL of Sf900II. Passage 2 (p2) recombinant baculoviruses were harvested on day 4 post infection and aliquoted as the Master Seed Stock, identified as BacNA1 P2 072817 and BacNA2 P2 072817.

Example 2: Verification of NA Activity in BacNA1 and BacNA2

The mature influenza NA protein is a tetrameric protein composed of four identical subunits. Mature NA has sialidase activity, cleaving sialic acid moieties on glycoproteins. Only mature, tetrameric protein has this enzymatic activity. To verify that the NA1 and NA2 genes expressed in baculovirus are enzymatically active, NA activity assays were performed.

NA activity is assayed using 2-o-(p-nitrophenyl)-α-D-N-acetylneuraminic acid (NP-NANA, SigmaAldrich N1516). For NA activity determination, 50 μL of 0.3 mM NP-NANA is combined with 50 μL of clarified culture supernatant and incubated in a flat-bottomed 96 well plastic plate for 1 hour at 37° C. before stopping the reaction with the addition of 100 μL of 1.0 N NaOH and measuring absorbance at 405 nm. As shown in FIG. 1, NA activity is confirmed by an absorbance >0.4 while supernatant from a control baculovirus culture has an absorbance <0.2. The control baculovirus culture is generated by culturing the baculovirus control strain, BacCon, under similar conditions. BacCon was constructed as described for Bac-NA1 and Bac-NA2 except pAcAB3 was used for transfection of Sf9 cells. BacCon does not contain a NA gene and establishes the background absorbance for baculovirus propagated in Sf9 cells.

Example 3: Protection Afforded Pigs Vaccinated with BacNA1 to a Heterologous H1N1 Challenge The experimental vaccine consisted of a crude mixture of Sf9 cells infected with the BacNA1 and culture supernatant inactivated with binary ethyleneimine formulated with 15% commercial oil-in-water adjuvant (CA50, Cambridge Technologies). Groups of eight, influenza seronegative three-week old pigs, acquired from Midwest Research Swine, were vaccinated with either inactivated BacNA1 culture fluids, an inactivated whole-virus H1N2 SIV or mock vaccinated. Vaccines were administered intramuscularly at four and six weeks of age. Pigs were challenged intranasally with 2 mL of 6.0 $TCID_{50}$/mL of a heterologous SIV A/swine/Minnesota/2073/2008 (H1N1). The challenge virus (α cluster) was heterologous both to the inactivated H1N2 vaccine group (γ cluster) as well as the recombinant NA1 (92% similarity).

Figure 2:
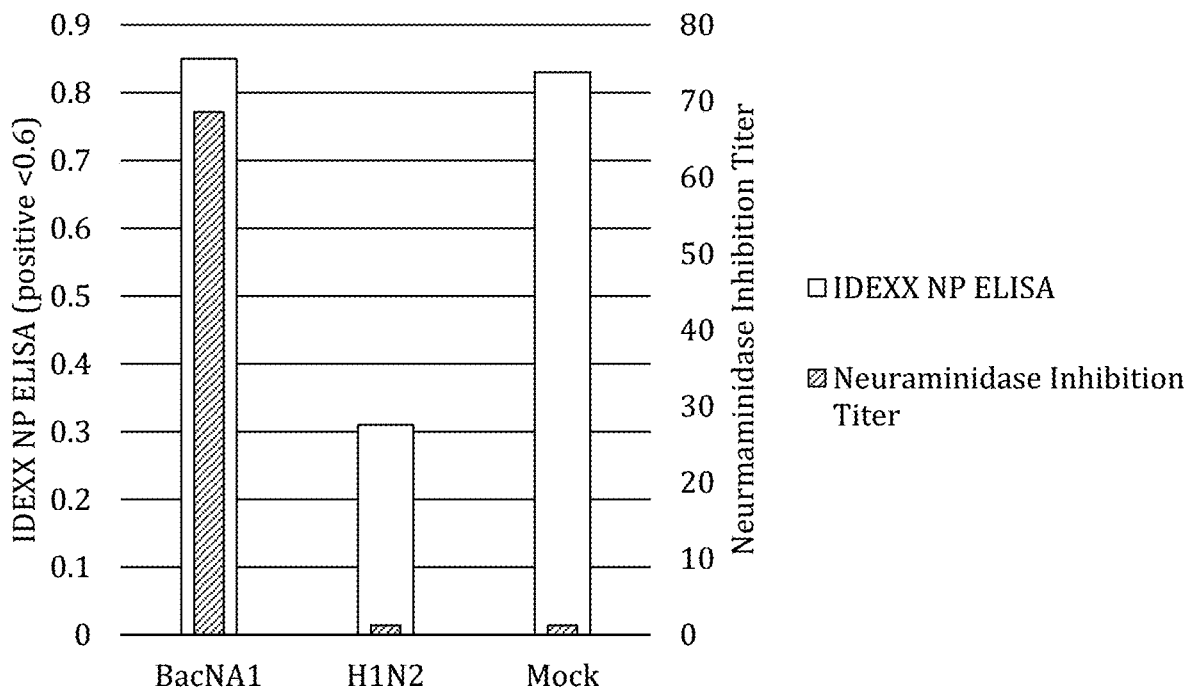
FIG. 2 is a graph showing the IDEXX IAV-S NP ELISA and NA inhibition (NI) titers in sera collected from pigs on the day of challenge.

Sera collected on the day of challenge was analyzed for α-IAV-S nucleoprotein antibodies using the commercially-available IDEXX ELISA assay. The IDEXX IAV-S NP ELISA and NA inhibition titers in sera collected from pigs on the day of challenge are shown in FIG. 2. All pigs inoculated with BacNA1 or mock vaccinated remained negative while pigs vaccinated with an inactivated H1N2 virus were positive (FIG. 2). Sera were also analyzed for NA inhibiting antibody titers using the challenge virus. Pigs vaccinated with BacNA1 had a mean NI titer of 69 while pigs in the other treatment groups were negative (FIG. 2).

Figure 3:
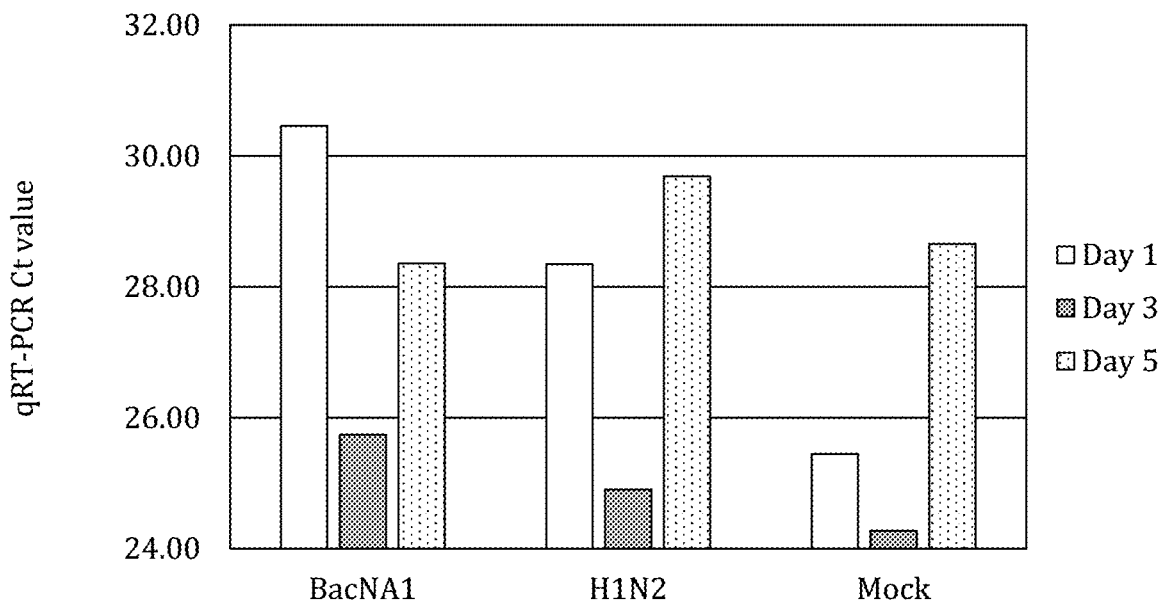
FIG. 3 is a graph of the qRT-PCR Ct values for Ct values in nasal swabs collected from pigs on days 1, 3 and 5 post-challenge.
Figure 4:
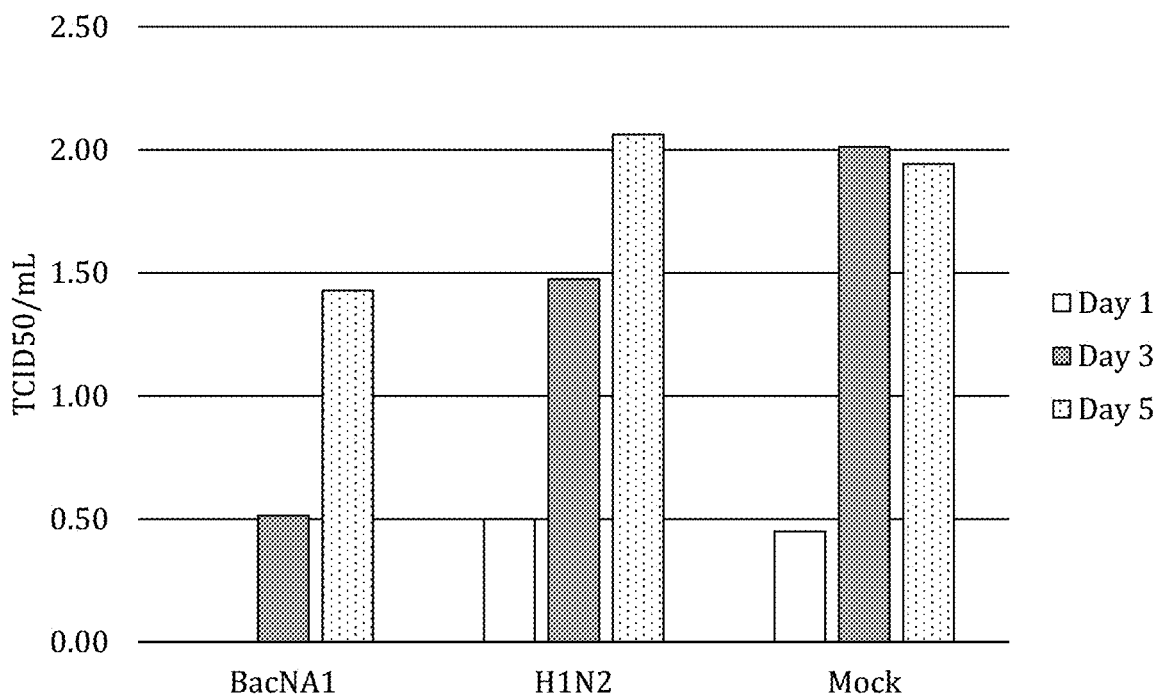
FIG. 4 is a graph of the SIV titers (TCID50/mL) in nasal swabs collected from pigs on days 1, 3 and 5 post challenge.

Nasal swabs were collected on the day of challenge and on days 1, 3 and 5 post-challenge. We employed two complementary approaches to detect viral shedding. The first approach was the standard qRT-PCR with the Cycle threshold (Ct) values as the readout, which are shown in FIG. 3 for Ct values in nasal swabs collected from pigs on days 1, 3 and 5 post-challenge. It is generally agreed that the higher Ct values, the lower amount of viral load. The second approach was cell-based $TCID_{50}$ experiment that measures the amount of infectious virus particles in nasal swabs. We used swine testicle (ST) cells for determining viral $TCID_{50}$. All pigs were negative for SIV on the day of challenge by qRT-PCR. Interestingly, we found that our N1-based recombinant vaccine offered better protection than the inactivated H1N2 vaccine. Specifically, we observed that Cycle threshold (CT) values for pigs vaccinated for BacNA1 were higher, representing lower levels of IAV-S shedding, on all three days (FIG. 3). FIG. 4 shows the SIV titers (TCID50/mL) in nasal swabs collected from pigs on days 1, 3 and 5 post challenge. Similar to the qRT-PCR results, lower amounts of IAV-S were detected in BacNA1 vaccinated pigs than pigs vaccinated with inactivated H1N2 virus or mock vaccinated (FIG. 4).

Figure 5:
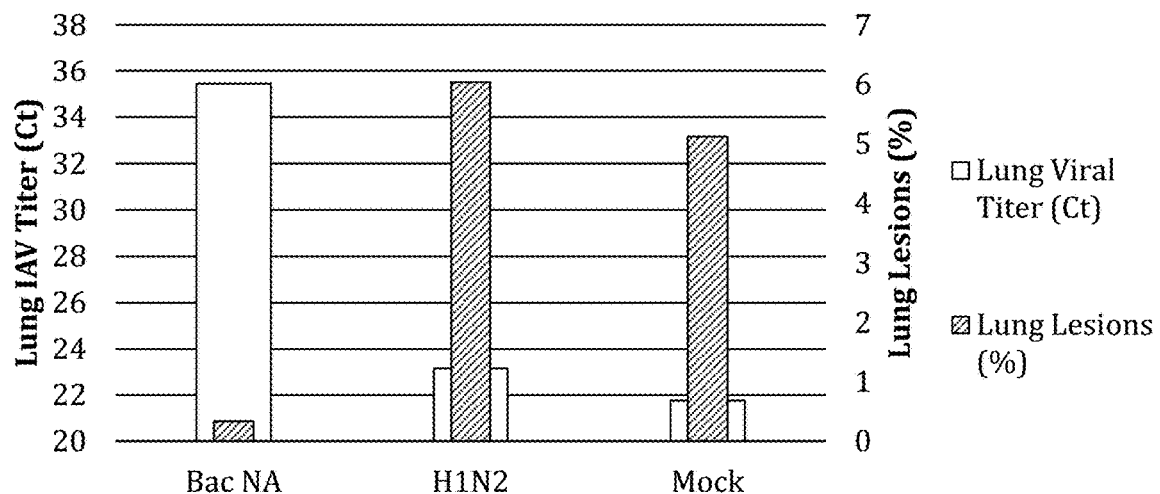
FIG. 5 is a graph of qRT-PCR Ct values and percent lung consolidation day 5 post challenge.

On day 5 post challenge, pigs were euthanized and the lungs were removed in toto and scored by a blinded veterinarian based on gross lung consolidation in each lobe (%) which was used to calculate total affected lung area. FIG. 5 shows the qRT-PCR Ct values and percent lung consolidation day 5 post challenge. Lung lesions were very low for BacNA1 vaccinated pigs (0.34%) while considerable lung consolidation was observed both for H1N2 and mock vaccinated pigs (6.0 and 5.1%, respectively, FIG. 5). A portion of the right cardiac lung was also analyzed for SIV by qRT-PCR. SIV was barely detectable for BacNA1 vaccinated pigs (Ct=35.4) while high viral loads were detected in the H1N2 and mock treatment groups (Ct's 23.1 and 21.8, respectively).

Figure 6:
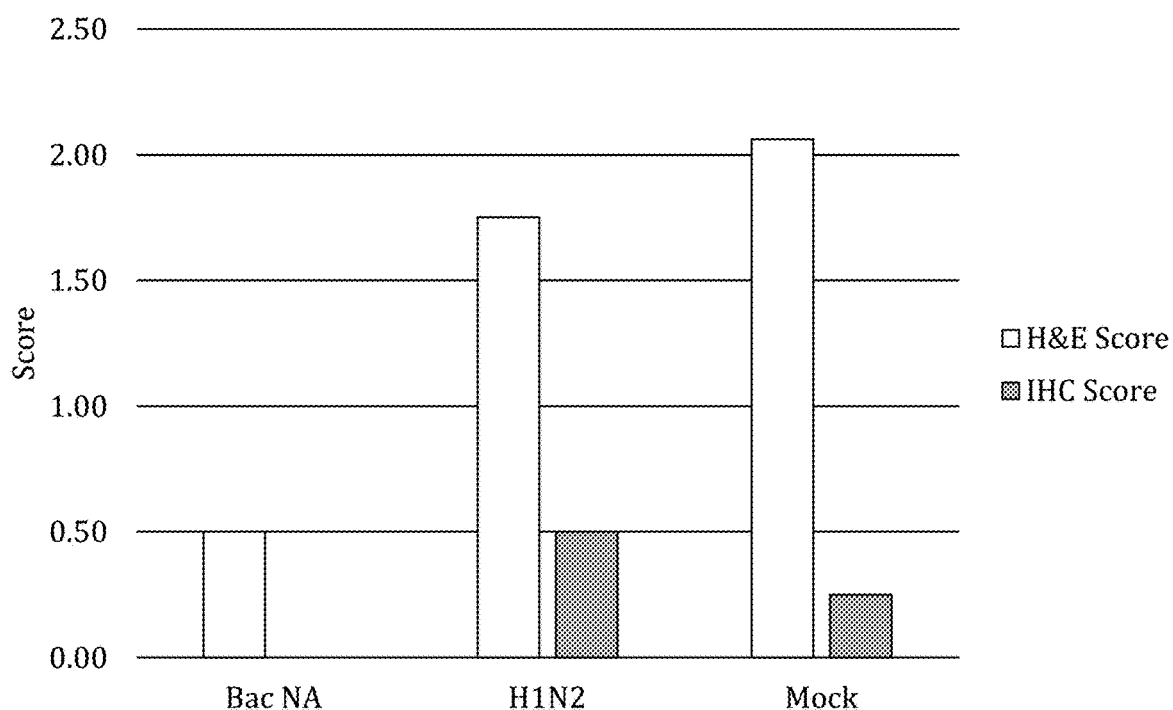
FIG. 6 is a graph of the pathology scores from lung tissue staining.

A portion of the right cardiac lobe was also fixed in formalin and analyzed for histopathology. Samples were scored on a 0-4 scale representing increased pathology based on hematoxylin and eosin staining and immunohistochemistry for SIV. Microscopic lung lesion scores based on hematoxylin and eosin (H&E) staining and immunohistochemistry (IHC) for IAV-S are shown in FIG. 6. The pathologist was blinded to the study design. Similar to the gross lung lesions, very little lung pathology was observed microscopically and SIV was not identified by IHC in BacNA1 vaccinated pigs (FIG. 6). In contrast, significantly more lung lesions along with associated IAV-S detection was observed in the H1N2 and mock treated pigs.

Example 4: Protection Afforded Pigs Vaccinated with BacNA1 and BacNA2 to a Heterologous H1N1 Challenge Baculovirus N1 and N2 cultures (two separate strains) were concentrated 10× by ultracentrifugation and used to formulate vaccines with straight antigen (0.85 mL N1 10× concentrate, 0.85 mL N2 10× concentrate, 0.3 mL CA50 adjuvant per dose) or 1:5 and 1:20 fold dilutions of the 10× antigen concentrate. Pigs vaccinated at 3 and 5 weeks of age and challenged at 7 weeks of age with a heterologous H1N1 (6 $TCID_{50}$/mL) which has a N1 protein ~92% similar to BacNA1.

Figure 7:
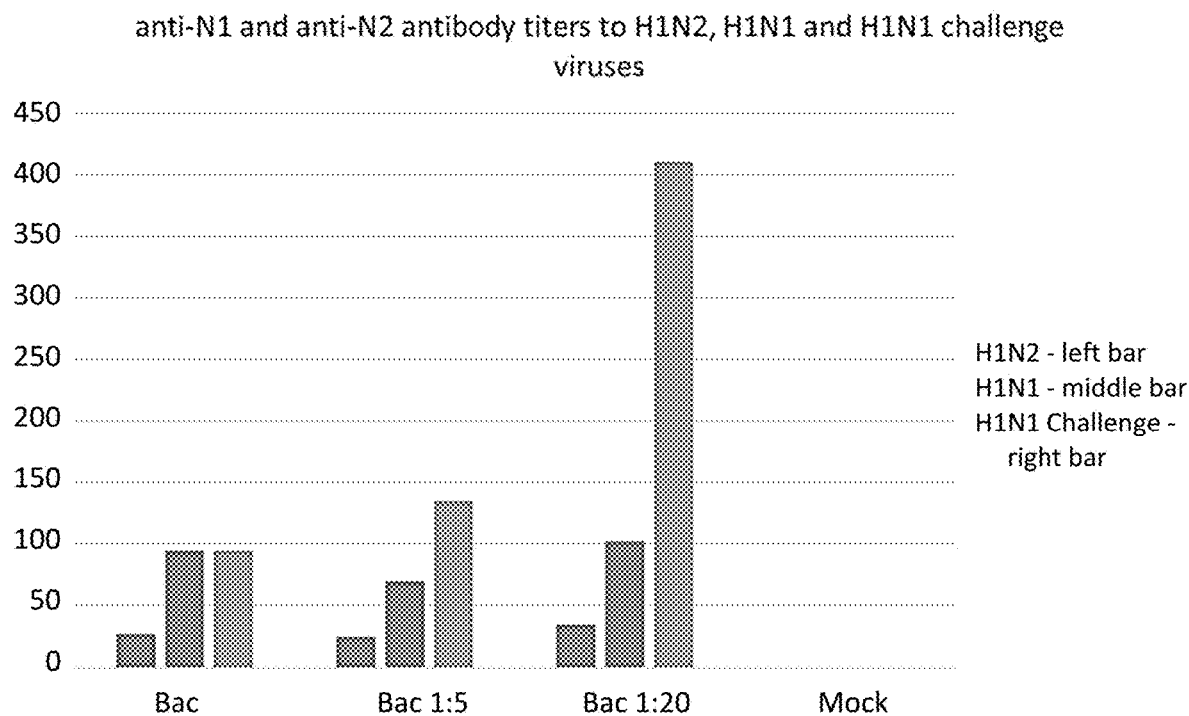
FIG. 7 is a graph of the results of the NA inhibition assay showing antibody generated to N1 and N2.
Figure 8:
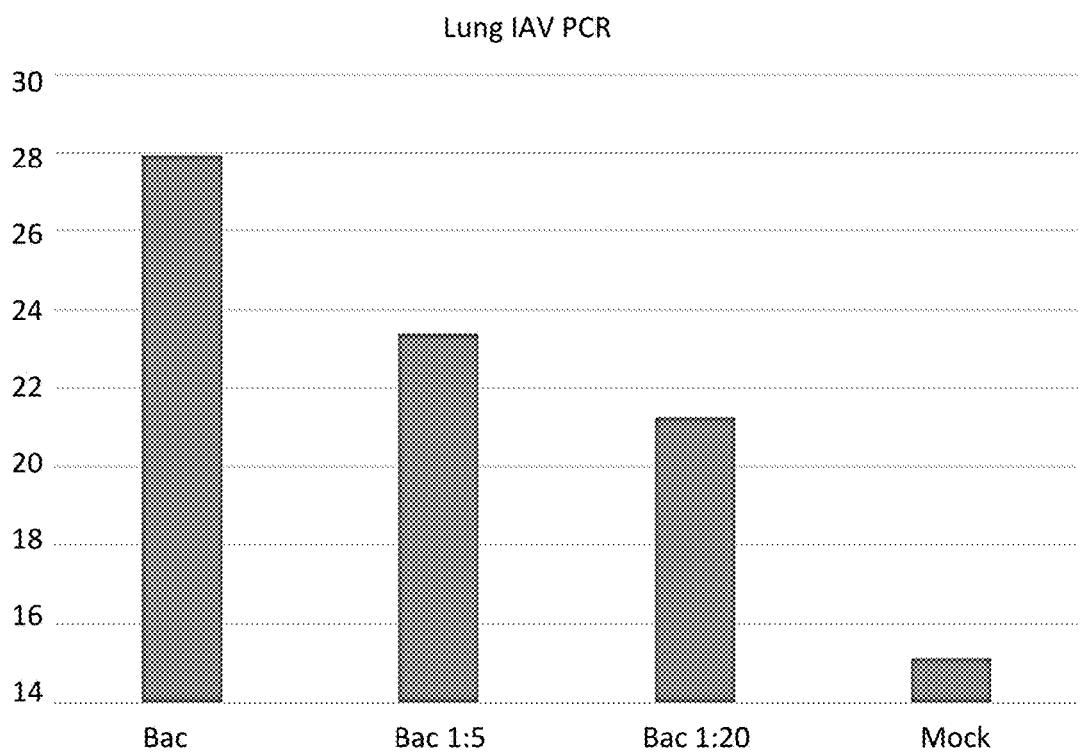
FIG. 8 is a graph of PCR results from lung tissue collected 5 days post-challenge with heterologous H1N1.
Figure 9:
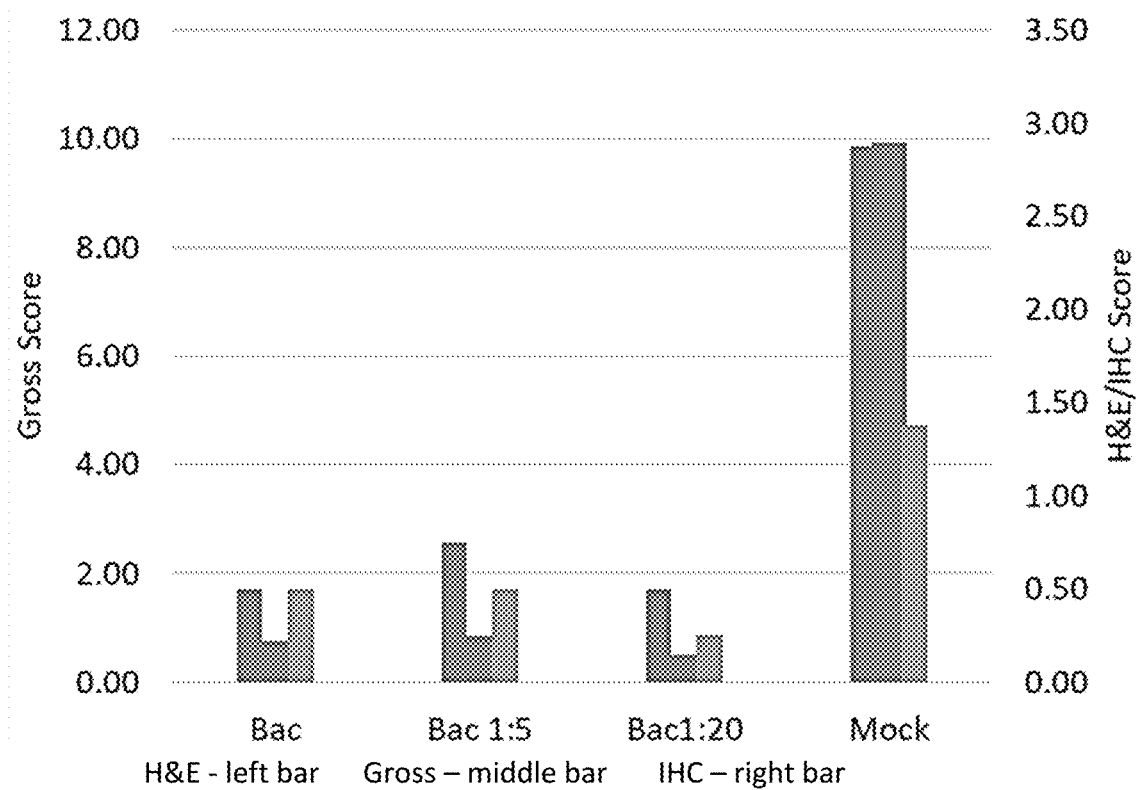
FIG. 9 is graph of gross and microscopic pathology scores on lungs collected 5 days post challenge.
Figure 10:
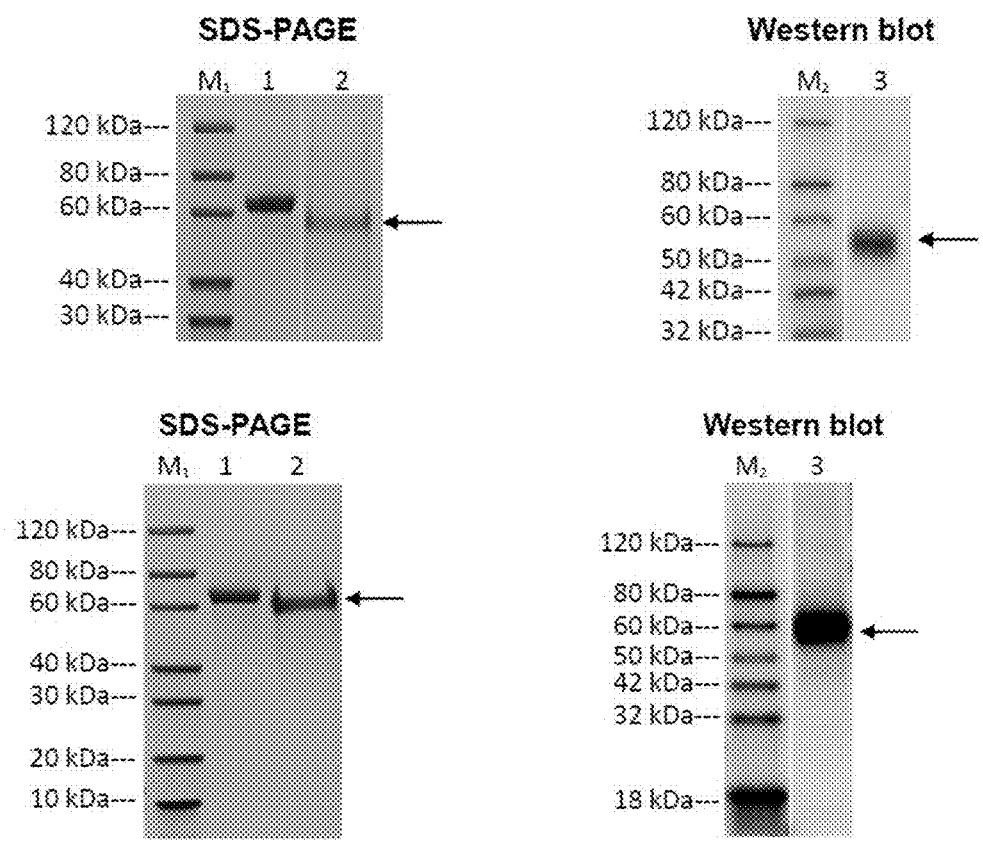
FIG. 10 shows images from SDS-PAGE and Western blotting of purified NA1 and NA2 proteins.

FIG. 7 shows the data from serology (NA inhibition assay) using parental H1N1 and H1N2 viruses as well as the challenge virus showing antibody generated to N1 and N2. Serum was collected from all pigs on the day of challenge. The NI assay results show that both BacNA1 and BacNA2 are able to stimulate an antibody response which is capable of inhibiting NA1 and NA2 activity. Importantly, antibodies generated against BacNA1 are able to cross react with the heterologous virus used for challenge.

FIG. 8 shows the results from PCR on lung tissue collected 5 days post challenge with heterologous H1N1. These results show a dose-dependent effect such that influenza virus titers in the lungs post-challenge are inversely correlated with the amount of antigen used for vaccination.

Gross and microscopic lung scores on lungs collected 5 days post challenge are shown in FIG. 9. These results demonstrate that all three vaccines formulations were capable of providing protection to lung damage caused by influenza virus infection. As the antigen pool used to generate the three vaccines was 10× concentrated baculovirus cultures, the vaccines represented approximately 8.5, 1.7 and 0.43 mL of BacNA1 and BacNA2 per dose.

Example 5: Quantification of NA Produced by BacNA1 and BacNA2

The full length native sequence of NA1 and NA2 expressed by BacNA1 and BacNA2, respectively, each contain an N-terminal transmembrane domain and consequently are found associated with Sf9 cellular or baculovirus lipid membranes. Membrane proteins are difficult to purify. In order to generate highly purified reference standards for NA1 and NA2 we expressed N-terminal truncated versions of NA1 (SEQ ID NO: 5) and NA2 (SEQ ID NO:6) in baculovirus which included the baculovirus GP67 secretion signal sequence to enable soluble protein expression. NA protein genes of A/swine/Iowa/A01782229/2016 (H1N1) and A/swine/Oklahoma/A01730659/2016 (H1N2) were synthesized such that the nucleotides encoding the N-terminal 35 amino acids were removed and replaced by the baculovirus Gp67 secretion signal peptide and a hexahistidine tag was added at the C-terminus of the protein (SEQ ID NO:5 and SEQ ID NO:6). The resulting genes were cloned into pAcAB3 and used to construct recombinant baculoviruses expressing soluble NA1 and NA2 as described in Example 1. Sf9 cell cultures of the resulting baculovirus strains were used to purify soluble NA1 and NA2 from the culture supernatant using affinity chromatography (immobilized Ni2+). The purified NA1 and NA2 proteins were visualized by SDS-PAGE and Western blotting using an antibody which recognizes the hexahistidine tag.

The purity of NA in each preparation was determined by densitometry of the SDS-PAGE gel to be >90%. In FIG. 10, Lane 1 contains 2 ug of bovine serum albumin standard as a reference. Lane 2 contains 2 ug of purified NA. Lane 3 contains 2 ug of purified NA. Protein concentration was determined by the Bradford assay using a bovine serum albumin standard curve. Purified NA1 was 0.21 mg/mL and NA2 was 0.14 mg/mL.

NA activity assays were performed on representative cultures of BacNA1 and BacNA1 along with purified, soluble NA1 and NA2 as described in Example 2. Parallel line analysis was performed on the NA activity assay curves to determine the concentration of NA1 and NA2 produced by BacNA1 and BacNA2, respectively, using the purified reference NA1 and NA2 of known concentration. Repeated measures of BacNA1 and BacNA2 cultures found approximately 50 µg/mL NA in both cultures.

Example 6. Protection Afforded Pigs Vaccinated with BacNA1 and BacNA2 to a Homologous H1N2 Challenge Baculovirus N1 and N2 cultures (two separate strains) were concentrated 10× by ultracentrifugation. The amount of NA present in the concentrated cultures were determined as described in Example 5. Vaccines were formulated to contain 200, 100, 50, 25 or 0 µg/dose of both NA1 and NA2 and 15% CA50 adjuvant. The dose volume was adjusted to 2 mL with phosphate buffered saline. Pigs were vaccinated at 3 and 5 weeks of age and challenged at 7 weeks of age with the homologous H1N2 (6 TCID50/mL) parental virus.

Figure 11:
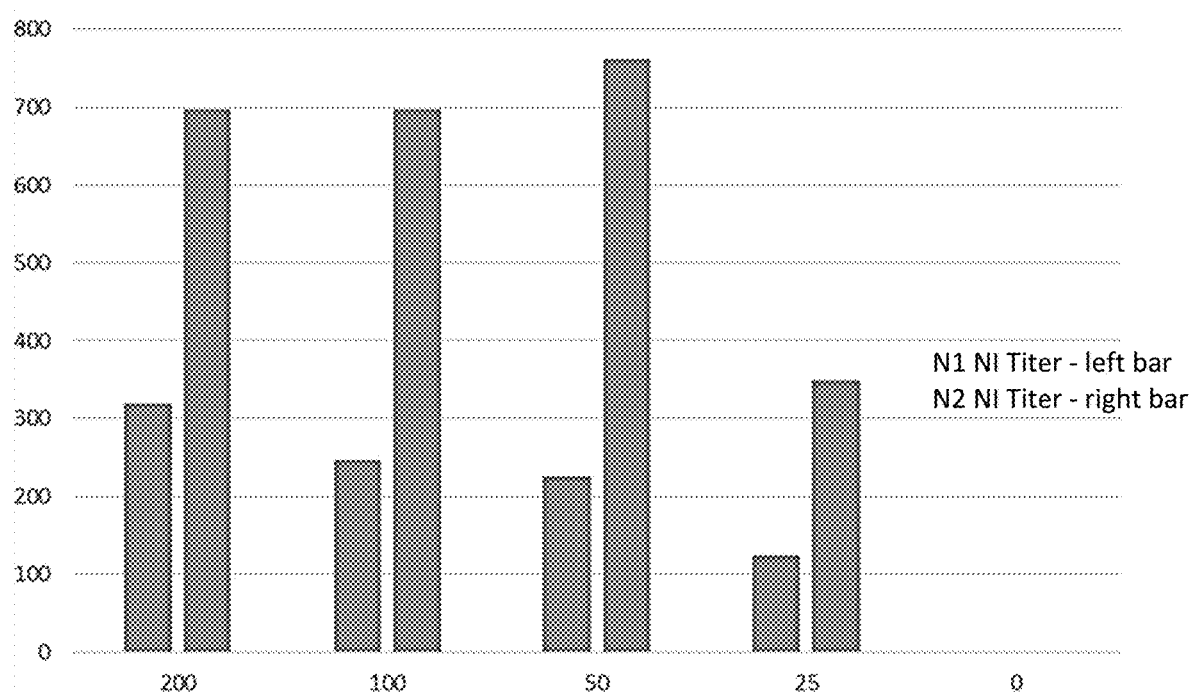
FIG. 11 is a graph of Serology-NA inhibition (NI) antibody titer to parental viruses.
Figure 12:
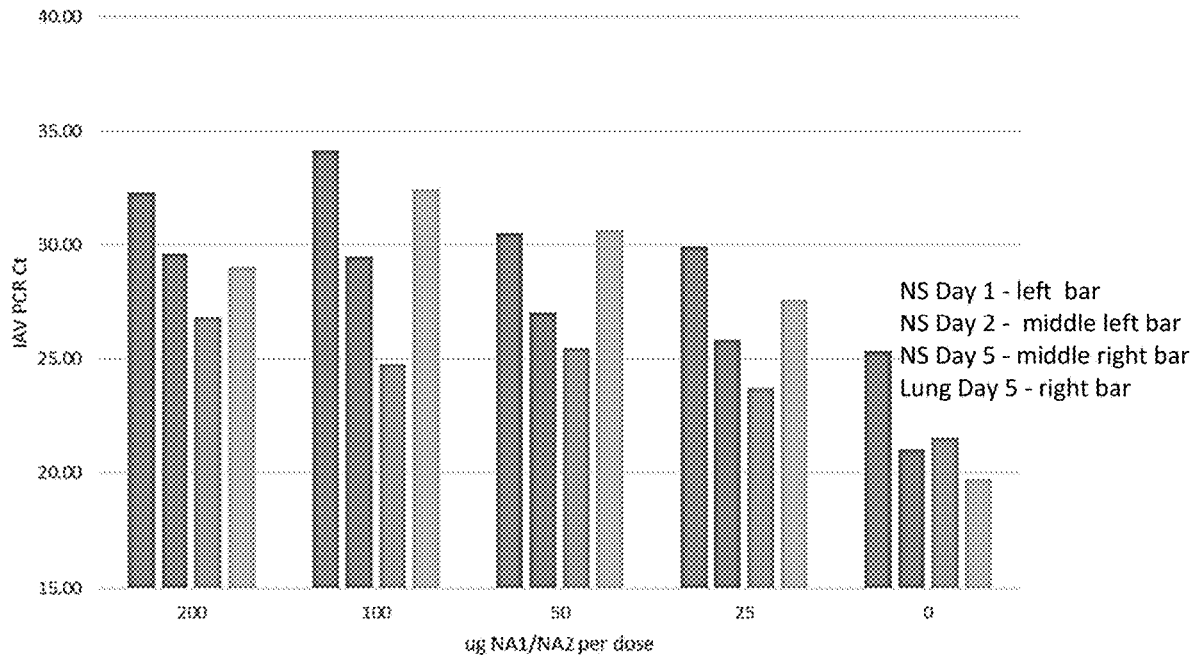
FIG. 12 is a graph of IAV PCR (Ct) values on nasal swabs collected on days 1, 2 and 5 post challenge and lung tissue collected day 5 post challenge.
Figure 13:
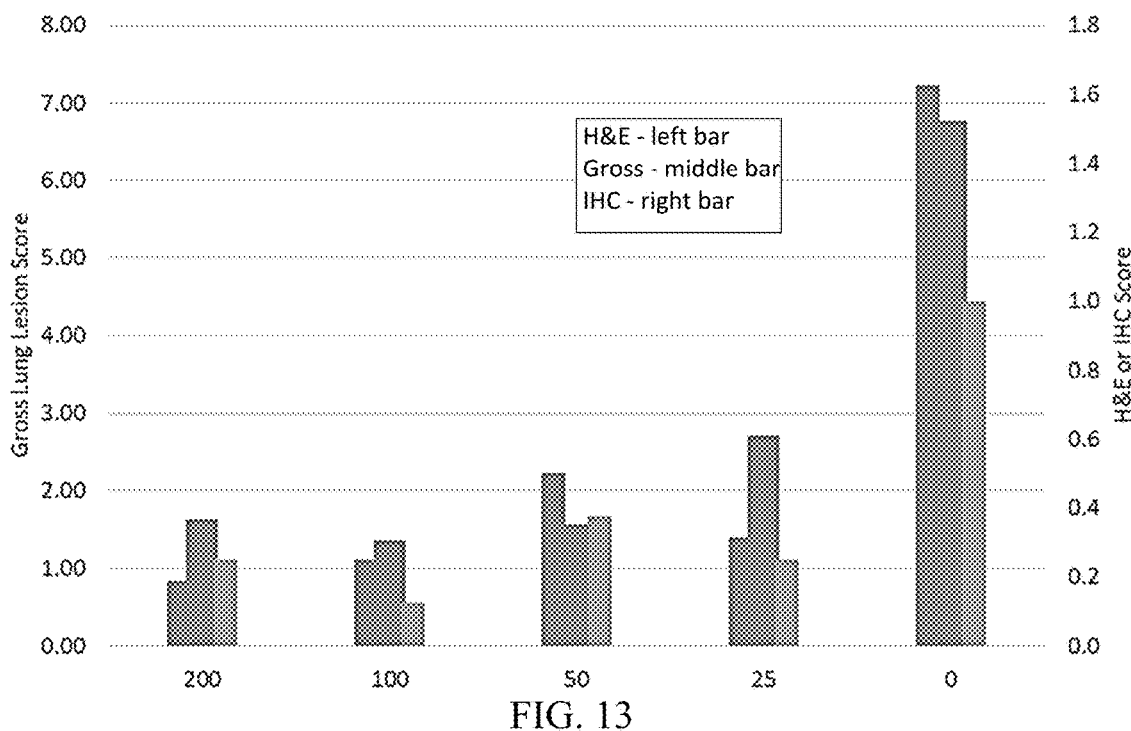
FIG. 13 is a graph of gross and microscopic scores on lung tissue collected day 5 post challenge.

Serology-NA inhibition antibody titer to parental viruses are shown in FIG. 11. All vaccine formulations induced antibody titers to both parental viruses. IAV PCR (Ct) values on nasal swabs collected on days 1, 2 and 5 post challenge and lung tissue collected day 5 post challenge are shown in FIG. 12. The amount of virus detected in nasal swabs and lungs were lower than mock vaccinated pigs at all time points. FIG. 13 includes the gross and microscopic scores on lung tissue collected day 5 post challenge. All vaccine formulations significantly reduced lung lesions.

Example 7. Protection Afforded Pigs Vaccinated with BacNA1 and BacNA2 to a Homologous H1N1 Challenge Baculovirus N1 and N2 cultures (two separate strains) were concentrated 10× by ultracentrifugation. The amount of NA present in the concentrated cultures were determined as described in Example 5. Vaccines were formulated to contain 200, 100, 50, 25 or 0 µg/dose of both NA1 and NA2 and 15% CA50 adjuvant. The dose volume was adjusted to 2 mL with phosphate buffered saline. Pigs were vaccinated at 3 and 5 weeks of age and challenged at 7 weeks of age with the homologous H1N1 (6 TCID50/mL) parental virus.

Figure 14:
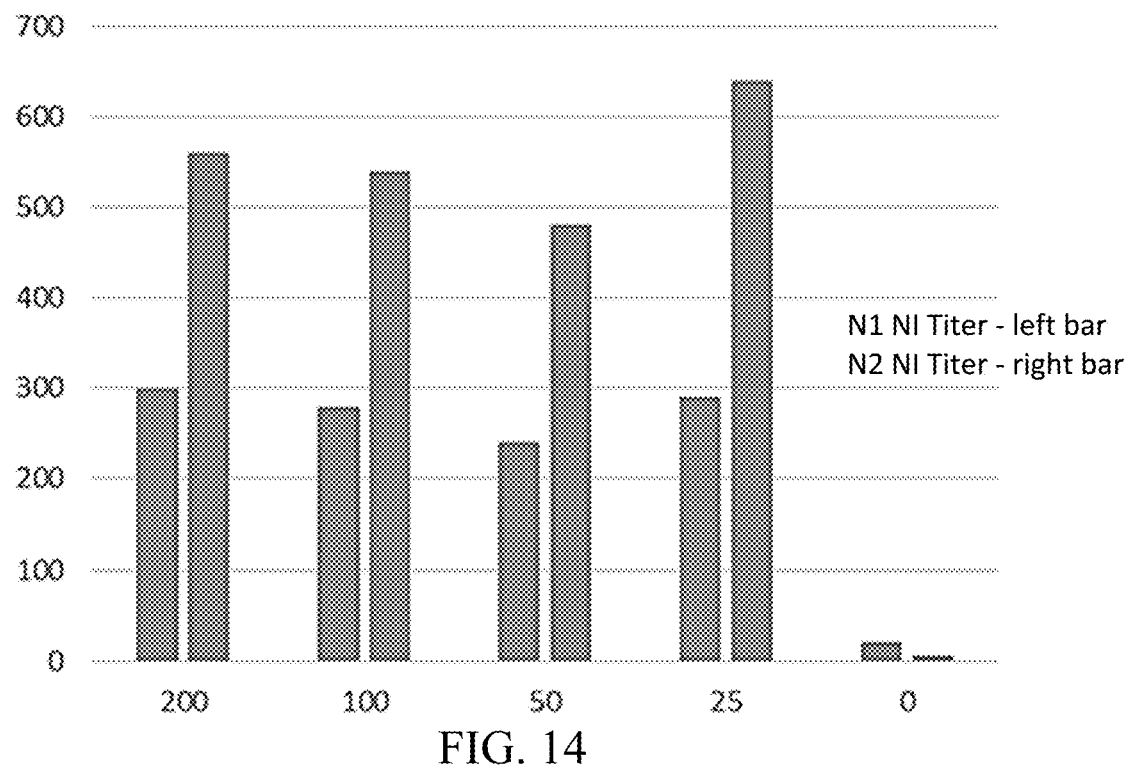
FIG. 14 is a graph of Serology-NA inhibition (NI) antibody titer to parental viruses.
Figure 15:
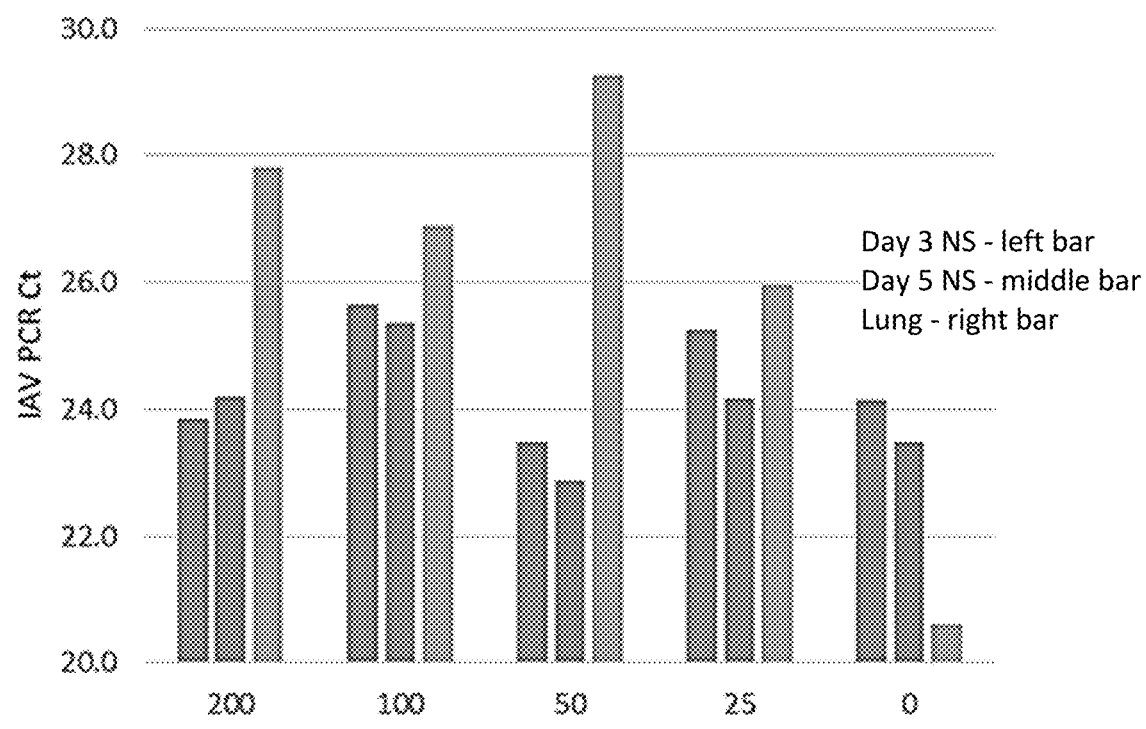
FIG. 15 is a graph of IAV PCR (Ct) values on nasal swabs collected on days 3 and 5 post challenge and lung tissue collected day 5 post challenge.
Figure 16:
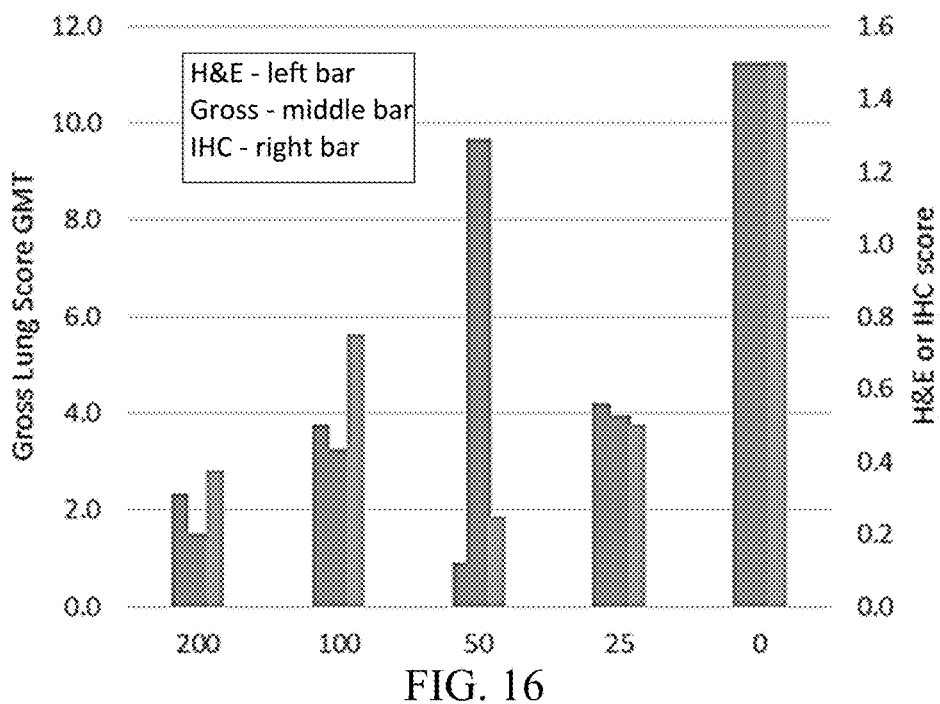
FIG. 16 a graph of gross and microscopic scores on lung tissue collected day 5 post challenge.

Serology-NA inhibition antibody titer to parental viruses are shown in FIG. 14. All vaccine formulations induced antibody titers to both parental viruses. The IAV PCR (Ct) values on nasal swabs collected on days 3 and 5 post challenge and lung tissue collected day 5 post challenge are shown in FIG. 15. While the amount of influenza detected in nasal swabs for vaccinated pigs was not significantly different than mock vaccinated pigs, all vaccine groups had significantly lower levels of influenza in lung samples. FIG. 16 shows the lung lesion scores GMT (geometric mean titer) as assessed by H&E and IHC staining were significantly reduced in all vaccine groups as compared to mock vaccinated pigs.

Example 8. Dose Titration Studies

Figure 17:
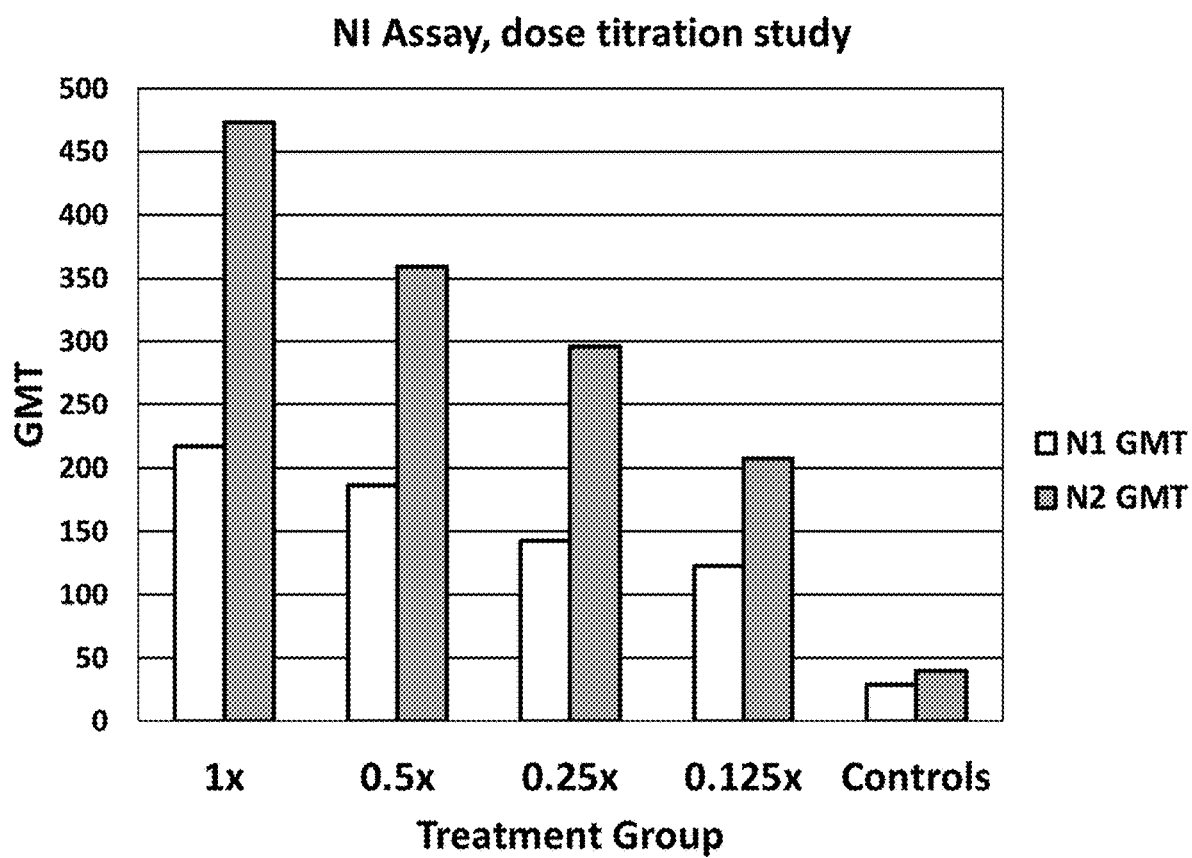
FIG. 17 is a graph of Serology-NA inhibition (NI) antibody titer to parental viruses for diluted vaccine formulations.
Figure 18:
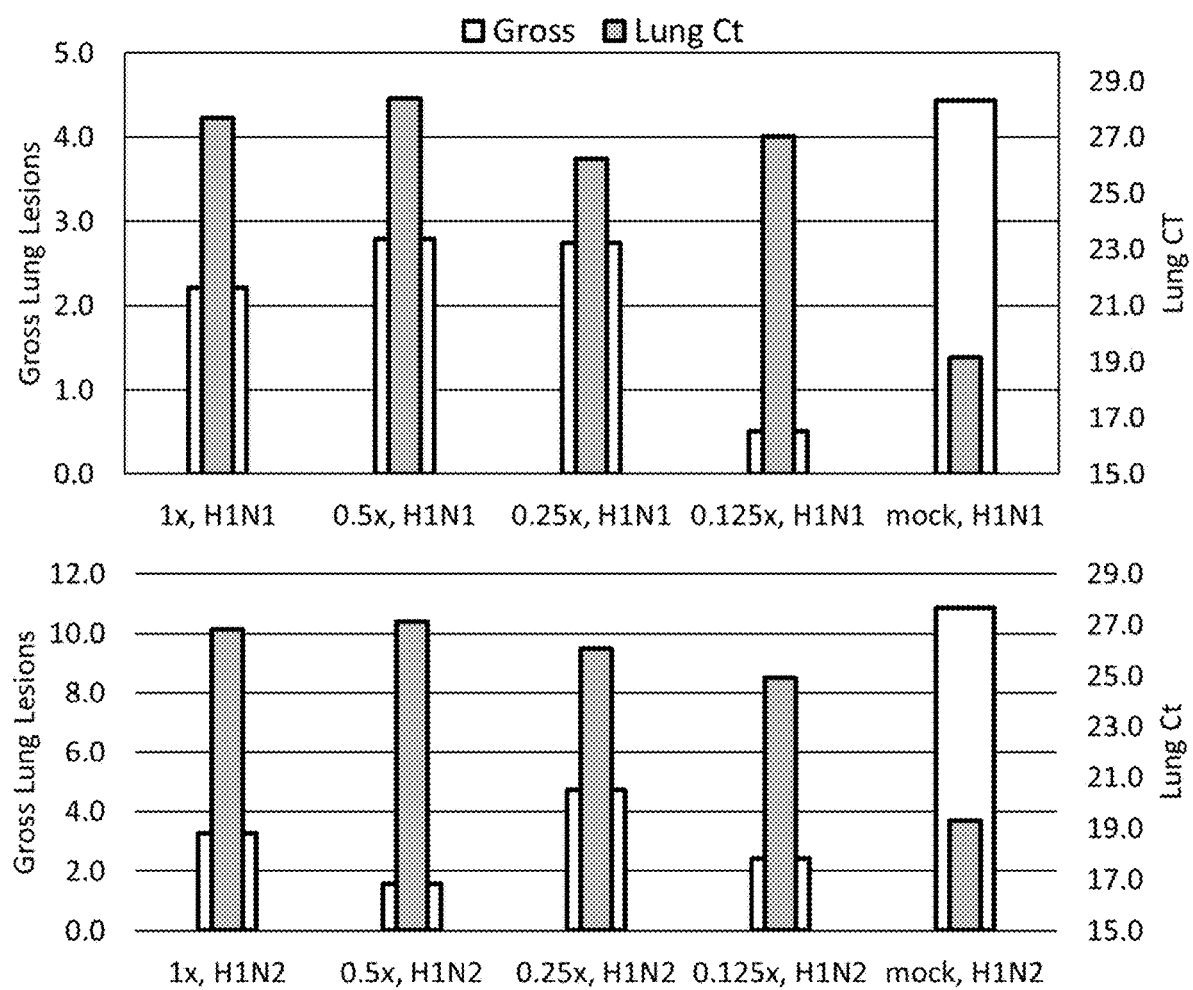
FIG. 18 shows graphs scoring gross lung lesions after challenge for pigs vaccinated with diluted vaccine formulations.
Figure 19:
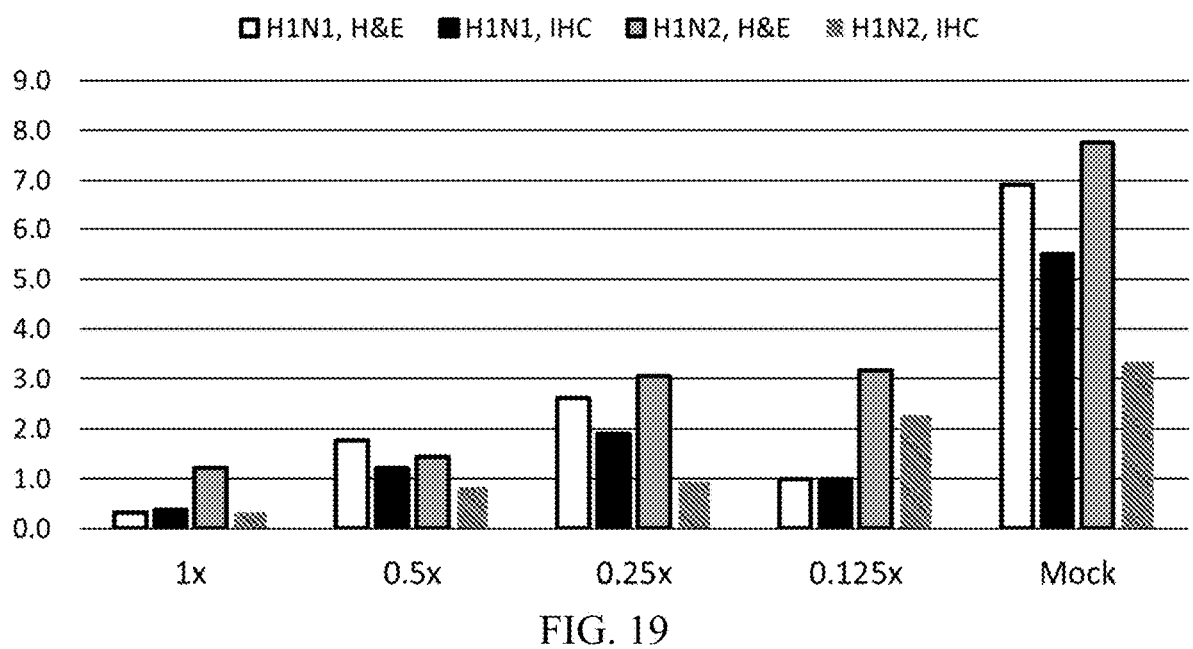
FIG. 19 shows a graph of IHC and H&E staining on lung tissue from pigs vaccinated with diluted vaccine formulations.

Further, dose titration studies were carried out. Pigs were vaccinated with crude baculovirus culture fluids as described at various dilution levels. The results are shown in FIG. 17-19. The 1× composition was formulated with 42.5 µg of NA1 and 42.5 µg of NA2 per dose. For the most dilute vaccine, 5 µg of NA1 and 5 µg of NA2 were enough antigen to give protection. FIG. 17 is a graph of serology using the NA inhibition assay. It clearly shows seroconversion for all vaccines and a successful dose response (decreasing antigen leading to lower NI titer). FIG. 18 shows the results of lung lesion scores for N1 and N2. FIG. 19 shows lung lesion scores as assessed by H&E and IHC staining were significantly reduced in all vaccine groups as compared to mock vaccinated pigs. These results demonstrate that the crude baculovirus culture fluids can be diluted ~8× and still be efficacious (~0.1 mL BacNA1/BacNA2 per dose).

Discussion

The results from these vaccination trials convincingly demonstrate that immunity based on influenza NA-alone provides significant protection from homologous and heterologous challenge. While NA-based immunity does not prevent infection, pigs were nearly completely protected from lung damage. Vaccination aimed at controlling viral dissemination in vivo may allow for the generation of infection immunity while mitigating clinical disease. Another exciting outcome of this study was the ability of recombinant NA1 to provide significant protection to a heterologous H1N1 challenge.

To date, only SIVs containing two NA subtypes (N1 or N2) infect the global swine industry and cause a significant economical concern. The NA genes of SIVs are less variable than the HA genes, which represents a good vaccine target. Currently FDA-approved inhibitors to treat human influenza are also targeting the functional NA protein. Including a HA component in the vaccines such as the marketed inactivated SIV vaccines will drive immune responses directed largely towards the immunodominant HA so antibody responses to NA with the universal protection potential will be masked or reduced.

---

The invention claimed is:

1. An immunogenic composition for inducing an immune response that mitigates clinical disease in swine from influenza after administration, said composition comprising recombinant baculovirus expression vectors in cultured insect cells dispersed in a pharmaceutically-acceptable carrier comprising insect cell culture media, optional adjuvant, said recombinant baculovirus expression vectors expressing a therapeutically effective amount of neuraminidase, said neuraminidase being associated with the cell membrane of said insect cells and/or baculovirus viral membrane surfaces in said composition and presented on the surfaces of said membranes.

2. The immunogenic composition of claim 1, wherein said clinical disease is lung damage or lung lesions in said swine.

3. The immunogenic composition of claim 2, wherein said lung damage or lung lesions are reduced in said swine.

4. The immunogenic composition of claim 1, wherein said clinical disease is reduced as measured by reduction in influenza viral titer in swine lung tissue.

5. The immunogenic composition of claim 1, wherein said swine is less than 8 weeks of age.

6. The immunogenic composition of claim 1, said recombinant baculovirus expression vectors expressing native, full-length neuraminidase protein.

7. The immunogenic composition of claim 1, said recombinant baculovirus expression vectors expressing neuraminidase derived from sequences of H1N1, H3N1, H1N2, H3N2, H5N1, H5N2, H3N8, and/or H3N2.

8. The immunogenic composition of claim 1, said composition comprising a first set of recombinant baculovirus expression vectors expressing neuraminidase subtype 1 and a second set of recombinant baculovirus expression vectors expressing neuraminidase subtype 2.

9. The immunogenic composition of claim 1, wherein the influenza antigenic components in said composition consists of influenza neuraminidase-type proteins.

10. The immunogenic composition of claim 1, wherein said composition is chemically inactivated.

11. The immunogenic composition of claim 1, wherein said composition is unpurified.

12. The immunogenic composition of claim 1, wherein said insect cells are *Spodoptera frugiperda* cells, *Trichoplusia ni* cells, *Bombyx mori* cells, or a cell line derived therefrom.

13. The immunogenic composition of claim 1, wherein said cell culture medium is serum free culture medium.

14. The immunogenic composition of claim 1, said pharmaceutically-acceptable carrier further comprising phosphate buffered saline.

15. The immunogenic composition of claim 1, in unit dosage form.

16. The immunogenic composition of claim 1, said composition being substantially free of influenza hemagglutinin.

17. The immunogenic composition of claim 1, said composition being substantially free of one or more of matrix proteins M1 or M2, RNA polymerase subunits PB1, PB2, and PA, nucleoprotein NP, nonstructural proteins NS1 or NS2, or associated virus like particles.

18. A kit for stimulating a universal immune response in swine against influenza infection, said kit comprising:
an immunogenic composition according to claim 1; and
instructions for administering said composition to a host swine animal susceptible to influenza.

19. A method of stimulating an immune response in swine that mitigates clinical disease from influenza infection, said method comprising administering an effective amount of an immunogenic composition according to claim 1 to swine less than 8 weeks of age, wherein maternal antibodies in said swine do not interfere with said immunogenic composition or immune response.

20. The method of claim 19, wherein said immune response mitigates clinical disease from homologous or heterologous influenza infection in said swine.

21. The method of claim 19, wherein said clinical disease is lung damage or lung lesions in said swine.

22. The method of claim 21, wherein said lung damage or lung lesions are reduced in said swine.

23. The method of claim 19, wherein said clinical disease is reduced as measured by reduction in influenza viral titer in lung tissue of said swine.

24. The method of claim 19 wherein said effective amount comprises a therapeutically effective amount of neuraminidase expressed in said composition.

25. The method of claim 19, said composition being administered intramuscularly, subcutaneously, intradermally, intravenously, or mucosally.

26. The method of claim 19, said immune response comprising production or activation of antibodies, B cells and/or T cells, directed specifically to neuraminidase in said host animal.

27. The method of claim 19, said immune response comprising production or activation of antibodies, B cells and/or T cells, directed to both neuraminidase subtype 1 and subtype 2 in said host animal.

28. The method of claim 19, wherein said immunogenic composition provides a protective immune response in said host animal against H1N1, H3N1, H1N2, H3N2, H5N1, H5N2, H3N8, and/or H3N2.

\* \* \* \* \*